(12) United States Patent
Legere et al.

(10) Patent No.: US 12,178,523 B2
(45) Date of Patent: Dec. 31, 2024

(54) COMPUTER ASSISTED SURGICAL NAVIGATION SYSTEM FOR SPINE PROCEDURES

(71) Applicant: GLOBUS MEDICAL, INC., Audubon, PA (US)

(72) Inventors: Douglas Legere, Haverhill, MA (US); Norbert Johnson, North Andover, MA (US); Gerd Schmieta, Boston, MA (US); Thomas Calloway, Pelham, NH (US); Dana Wisniewski, Audubon, PA (US); Dale Earle, Derry, NH (US); Ryan Fischer, Billerica, MA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 168 days.

(21) Appl. No.: 17/656,522

(22) Filed: Mar. 25, 2022

(65) Prior Publication Data

US 2023/0081244 A1   Mar. 16, 2023

Related U.S. Application Data

(60) Provisional application No. 63/176,424, filed on Apr. 19, 2021.

(51) Int. Cl.
| | |
|---|---|
| *A61B 34/20* | (2016.01) |
| *A61B 34/10* | (2016.01) |
| *A61B 90/00* | (2016.01) |

(52) U.S. Cl.
CPC .............. *A61B 34/20* (2016.02); *A61B 34/10* (2016.02); *A61B 2034/2055* (2016.02); *A61B 2090/363* (2016.02); *A61B 2090/376* (2016.02)

(58) Field of Classification Search
CPC ...... A61B 2034/2055; A61B 2090/363; A61B 34/25; A61B 2090/3983; A61B 34/20; A61B 34/10

See application file for complete search history.

(56) References Cited

U.S. PATENT DOCUMENTS

| | | |
|---|---|---|
| 4,150,293 A | 4/1979 | Franke |
| 5,246,010 A | 9/1993 | Gazzara et al. |

(Continued)

FOREIGN PATENT DOCUMENTS

| | | |
|---|---|---|
| EP | 2676627 A2 | 12/2013 |
| EP | 3431032 A1 | 1/2019 |

(Continued)

OTHER PUBLICATIONS

US 8,231,638 B2, 07/2012, Swarup et al. (withdrawn)

*Primary Examiner* — Serkan Akar
*Assistant Examiner* — Felix A Donis-Barrera

(57) ABSTRACT

A surgical system for computer assisted navigation during surgery, includes at least one processor that obtains a 3D radiological representation of a targeted anatomical structure of a patient and a set of fiducials of a registration fixture. The operations attempt to register locations of the set of fiducials in the 3D radiological representation to a 3D imaging space tracked by a camera tracking system. Based on determining one of the fiducials of the set has a location that was not successfully registered to the 3D imaging space, the operations display at least one view of the 3D radiological representation with a graphical overlay indicating the fiducial has not been successfully registered to the 3D imaging space, receive user-supplied location information identifying where the fiducial is located in the 3D radiological representation, and register the location of the fiducial to the 3D imaging space based on the user-supplied location information.

17 Claims, 27 Drawing Sheets

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |

(56) References Cited

U.S. PATENT DOCUMENTS

| | | |
|---|---|---|
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |

(56) References Cited

U.S. PATENT DOCUMENTS

| | | |
|---|---|---|
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 11,553,969 B1 * | 1/2023 | Lang .................. G06T 7/0012 |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |

(56) References Cited

U.S. PATENT DOCUMENTS

| | | |
|---|---|---|
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |

(56) References Cited

U.S. PATENT DOCUMENTS

| | | |
|---|---|---|
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0209225 A1* | 7/2017 | Wu ................. A61B 6/032 |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2019/0209080 A1* | 7/2019 | Gullotti ............ A61B 17/7035 |
| 2020/0197102 A1* | 6/2020 | Shekhar ............ A61B 8/4245 |
| 2020/0253640 A1* | 8/2020 | Mullaney ............ G06T 7/74 |
| 2021/0045813 A1 | 2/2021 | Wickham et al. |

FOREIGN PATENT DOCUMENTS

| | | | | |
|---|---|---|---|---|
| JP | 2019022658 A | | 2/2019 | |
| JP | 2020096795 A | | 6/2020 | |
| KR | 20200109292 A | * | 9/2020 | ............ A61C 9/004 |
| WO | WO-2020163316 A1 | * | 8/2020 | ............ A61B 34/10 |
| WO | WO-2021062001 A1 | * | 4/2021 | ......... A61B 17/7082 |
| WO | WO-2021062373 A2 | * | 4/2021 | ......... A61B 17/1615 |

* cited by examiner

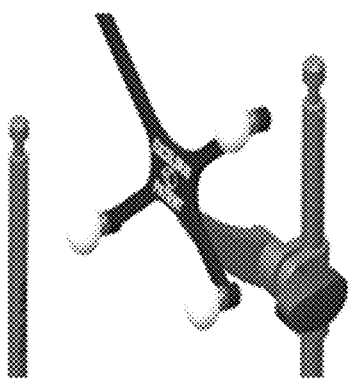 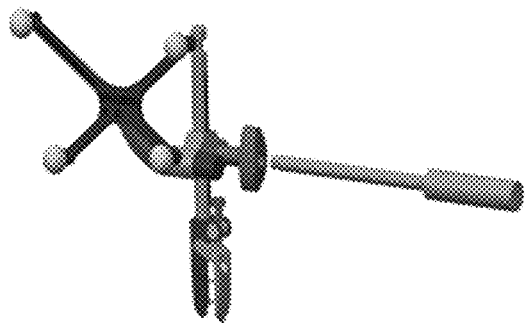
Figure 7　　　　　　　　　　Figure 8
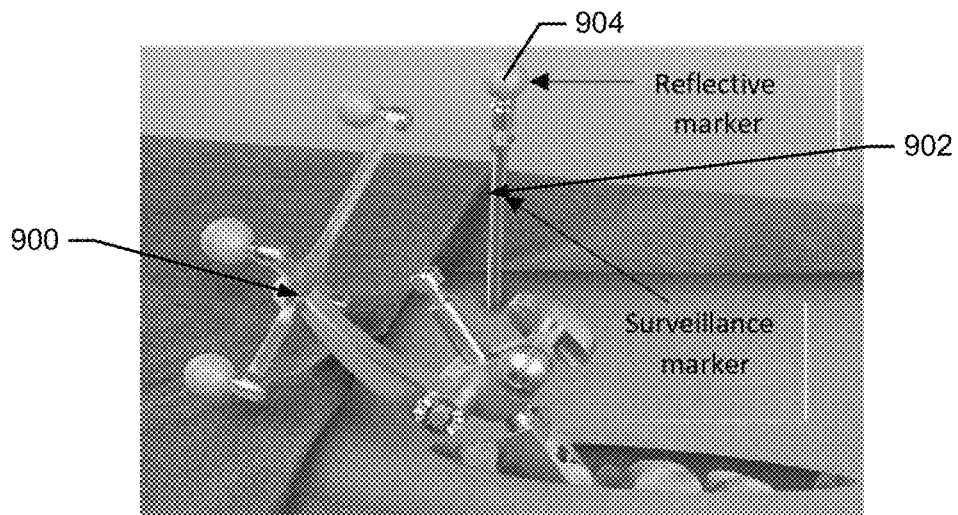
Figure 9
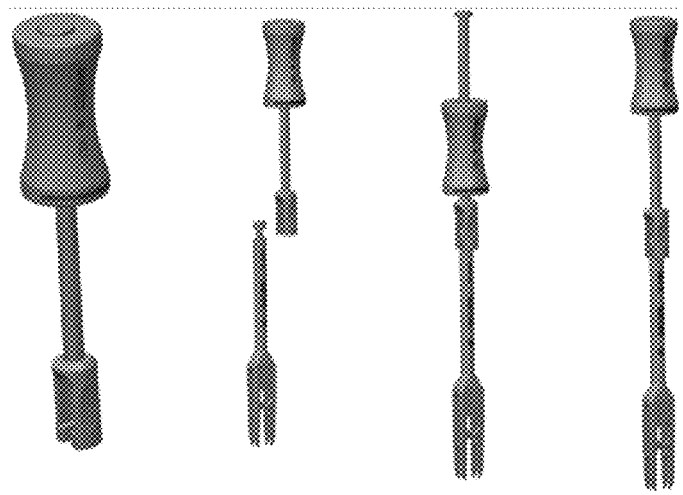
Figure 10

COMPUTER ASSISTED SURGICAL NAVIGATION SYSTEM FOR SPINE PROCEDURES

RELATED APPLICATIONS

This application claims the benefit of U.S. provisional patent application Ser. No. 63/176,424, filed Apr. 19, 2021, the disclosure of which is hereby incorporated herein by reference in its entirety.

TECHNICAL FIELD

The present disclosure relates to computer assisted navigation of equipment and operations during surgery.

BACKGROUND

Surgical operating rooms can contain a diverse range of medical equipment, which can include computer assisted surgical navigation systems, medical imaging devices (e.g., computerized tomography (CT) scanners, fluoroscopy imaging, etc.), surgical robots, etc.

A computer assisted surgical navigation system can provide a surgeon with computerized visualization of the present pose of a surgical tool relative to medical images of a patient's anatomy. Camera tracking systems for computer assisted surgical navigation typically use a set of cameras to track pose of a reference array on a surgical tool, which is being positioned by a surgeon during surgery, relative to a patient reference array (also "dynamic reference base" (DRB)) attached to a patient. The reference arrays allow the camera tracking system to determine a pose of the surgical tool relative to anatomical structure imaged by a medical image of the patient and relative to the patient. The surgeon can thereby use real-time visual feedback of the pose to navigate the surgical tool during a surgical procedure on the patient.

Many surgical workflows using computer assisted surgical navigation systems require image scans, such as CT scans or magnetic resonance imaging scans, during the surgical procedure. Perpendicular scan slices (axial, sagittal, and coronal) may be used to enable operators to visualize the patient's anatomy alongside the relative poses of surgical instruments. The surgical workflows may be challenging for surgeons and other surgical team members to recall, interpret, and follow under the time constraints and other pressures of a surgery environment. Improved surgical workflows and computer implemented operations to reduce the workload on the surgery team and to ensure processes and best practices are followed.

SUMMARY

Some embodiments of the present disclosure are directed to a surgical system for computer assisted navigation during surgery. The surgical system includes at least one processor that is operative to obtain a three-dimensional (3D) radiological representation of a targeted anatomical structure of a patient and a set of fiducials of a registration fixture. The operations attempt to register locations of the set of fiducials in the 3D radiological representation to a 3D imaging space tracked by a camera tracking system. Based on determining one of the fiducials of the set has a location that was not successfully registered to the 3D imaging space, the operations display at least one view of the 3D radiological representation with a graphical overlay indicating the fiducial has not been successfully registered to the 3D imaging space, receive user-supplied location information identifying where the fiducial is located in the 3D radiological representation, and register the location of the fiducial to the 3D imaging space based on the user-supplied location information.

In some further embodiments, the operation to attempt to register locations of the set of fiducials in the 3D radiological representation to the 3D imaging space tracked by the camera tracking system, includes to obtain, from at least one camera of the camera tracking system, an optical image of a reference array fixated to the patient. The reference array includes a set of optical markers detectable by the at least one camera of the camera tracking system in the 3D imaging space. The operations attempt to register locations of a pattern of the set of optical markers to locations of a pattern of the set of fiducials in the 3D radiological representation, and identify any of the optical markers of the reference array that are not successfully registered to any of the fiducials of the registration fixture.

In some further embodiments, the operations include to display a virtual implant device as an overlay on a view of the 3D radiological representation of the targeted anatomical structure. The operations display a graphical indication of a trajectory of the virtual implant device representing an implantation trajectory of the virtual implant device into the targeted anatomical structure. The operations update pose of the graphical indication of the trajectory of the virtual implant device displayed in the view of the 3D radiological representation, to track steering inputs received through a user interface of the surgical system. The operations store as a planned trajectory of the virtual implant device, a user-designated one of the poses of the graphical indication of the trajectory.

In some further embodiments, prior to obtaining the 3D radiological representation of the targeted anatomical structure of the patient and the set of fiducials of the registration fixture, the operations include to obtain, from at least one camera of the camera tracking system, optical images of a reference array fixated to the patient and of a registration fixture attached to a radiological imaging device. The reference array includes a first set of optical markers detectable by the at least one camera of the camera tracking system in the 3D imaging space, and the registration fixture includes a second set of optical markers detectable by the at least one camera of the camera tracking system in the 3D imaging space. The operations obtain a fluoroscopic image of the targeted anatomical structure of the patient and the set of fiducials of the registration fixture. The operations determine whether a first condition is satisfied based on a defined number of the optical markers in the first set being detected by the at least one camera of the camera tracking system in the 3D imaging space. The operations determine whether a second condition is satisfied based on a defined number of the optical markers in the second set being detected by the at least one camera of the camera tracking system in the 3D imaging space. The operations determine whether a third condition is satisfied based on a defined number of the set of fiducials of the registration fixture being visible in the fluoroscopic image. When one of the first, second, and third conditions is not satisfied, the operations display an indication of the not satisfied one of the first, second, and third conditions, and inhibit capture by a radiological imaging process of the 3D radiological representation of the targeted anatomical structure of the patient and the set of fiducials of the registration fixture. In contrast, when each of the first, second, and third conditions are satisfied, the operations enable capture by the radiological imaging process of the 3D radiological representation of the targeted anatomical structure of the patient and the set of fiducials of the registration fixture.

Still other surgical systems, methods, and computer program products according to embodiments of the inventive subject matter will be or become apparent to one with skill in the art upon review of the following drawings and detailed description. It is intended that all such surgical systems, methods, and computer program products be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings:

FIG. 7 illustrates a process for securing a Dynamic Reference Base (DRB) to a patient attachment instrument according to some embodiments;

FIG. 8 illustrates a process for tightening a DRB knob using a clamp driver according to some embodiments;

FIG. 9 illustrates a placement of a DRB and surveillance marker according to some embodiments;

FIG. 10 illustrates a process for removing a quattro spike with removal tool according to some embodiments;

DETAILED DESCRIPTION

Figure 1:
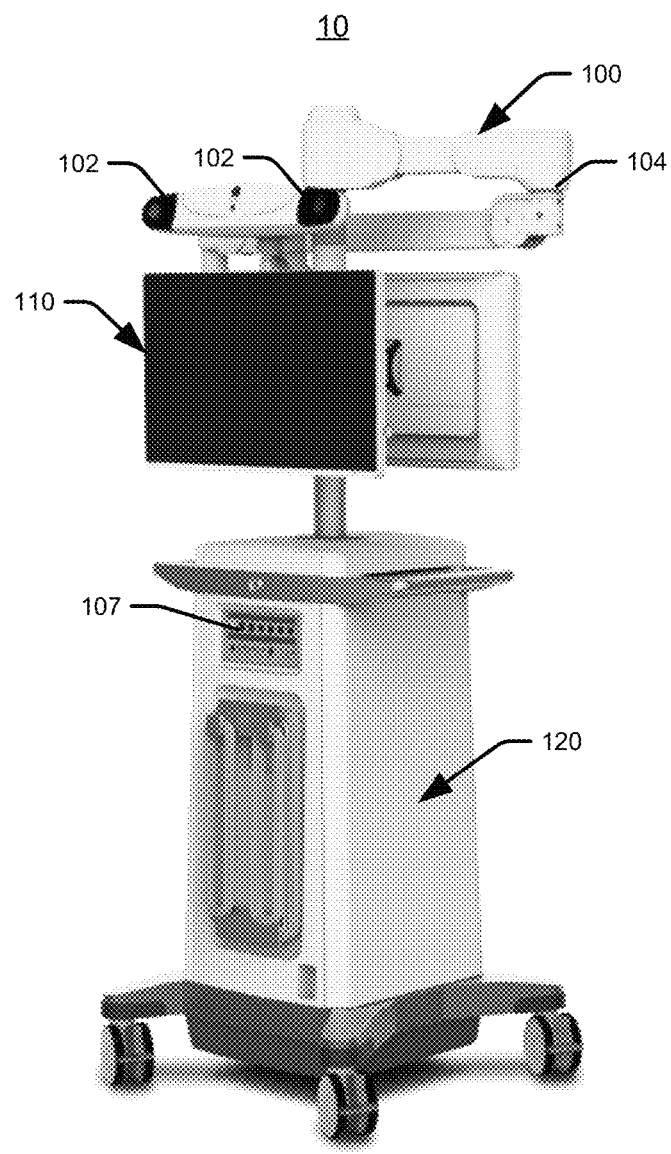
FIG. 1 illustrates the ExcelsiusHub components according to some embodiments.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

System Overview

The ExcelsiusHub, by Globus Medical, Inc. (hereinafter "Globus Medical" or "Globus"), enables real-time surgical navigation and visualization using radiological patient images, and guides compatible surgical instruments to a precise location and trajectory based on implant planning or provides visualization for assisting with free-hand navigation. The software reformats patient-specific CT images acquired before or during surgery, or fluoroscopic images acquired during surgery, and displays them on-screen based on the preferred perspective. Prior to operating, the surgeon may create, store, access, and simulate instrument and other trajectories relative to patient anatomy captured in the CT images. During surgery, the system recognizes the instrument in use and aids the user by way of free-hand navigation to place implants with consistent accuracy. ExcelsiusHub tracks the position of surgical instruments in or on the patient anatomy, and continuously updates the instrument position on these images. The surgery is performed by the surgeon, using various Globus Medical specialized surgical instruments.

Although various embodiments are described in the context of operational extensions to Excelsius system products and other Globus Medical products, these and other embodiments are not limited thereto and can be used with any surgical procedure navigation system.

Device Description

The ExcelsiusHub is a surgical procedure navigation system that enables real-time surgical visualization using radiological patient images (e.g., preoperative CT, intraoperative CT and/or fluoroscopy), a patient dynamic reference base, and an advanced camera tracking system. The system is mapped based on the registration between the virtual patient (points on the patient images) and the physical patient (corresponding points on the patient's anatomy). Once this registration is created, the software displays the relative position of a tracked instrument on the patient images. This visualization can help guide the surgeon's planning and approach for implant placement and other surgical procedures. The patient's scan coupled with the registration provides guidance assistance to the surgeon when using the system independently for free hand navigation or can provide robotic guidance and align the end effector when used with the ExcelsiusGPS Robotic System. During surgery, the system uses the camera tracking system to track the position of compatible instruments, including the end effector on the robotic arm, in or on the patient anatomy and continuously updates the instrument position on patient images utilizing optical tracking. System software may be responsible for navigation functions, data storage, network connectivity, user management, case management, and safety functions. The ExcelsiusHub surgical instruments are typically non-sterile, re-usable instruments that can be operated manually.

The ExcelsiusHub freehand instrumentation includes registration instruments, patient reference instruments, and implant-specific surgical instruments. The system can also be used with the ExcelsiusGPS robotic system, including actively tracked end-effectors. Registration instruments have incorporated arrays of reflective markers, which are used to track patient anatomy and surgical instruments and implants. Components include the verification probe, surveillance marker, surgical instrument arrays, intra-op CT registration fixture, fluoroscopy registration fixture, and dynamic reference base (DRB). Patient reference instruments are either clamped or driven into any appropriate rigid anatomy that is considered safe and provides a point of rigid fixation for the DRB. Surgical instruments are used to prepare the implant site or implant the device, and include awls, drills, drivers, taps, and probes.

Indications for Use

The ExcelsiusHub can be used as an aid for precisely locating anatomical structures in open or percutaneous procedures and for precisely positioning compatible surgical instruments or implants during surgery. The ExcelsiusHub is indicated for any medical condition in which the use of stereotactic surgery may be appropriate, and where reference to a rigid anatomical structure, such as the spine or pelvis, can be identified relative to a CT, X-ray, and/or MRI based model of the anatomy. The ExcelsiusHub supports pre-operative CT, intra-operative CT, and/or intra-operative Fluoroscopic procedures.

Further System Overview

The ExcelsiusHub Visualization System provides stand-alone navigation and guidance for previously cleared posterior fixation and interbody implant placement. The ExcelsiusHub can operate with the ExcelsiusGPS Robotic System to provide camera and tracking system functionality. The ExcelsiusHub can also provide a universal viewing station and registration operations for intraoperative mobile CT systems. Excelsius enabling technologies can be supported and communicate through the ExcelsiusHub, which can provide desired integral components for operating rooms.

Hardware

A camera tracking system 200 The ExcelsiusHub components can be divided into three subassemblies as shown in FIG. 1: a camera arm assembly 100, a display assembly 120, and a housing base assembly 130, according to some embodiments. The camera arm assembly 100 includes spaced apart stereo cameras 102 and an articulating arm 104. The housing base assembly 130 includes a processing platform with at least one processor and memory, an input and/or output user interface, and communication circuitry which is configured to communicate through wired (e.g., connector panel 107) and/or wireless connections with other system components. The cameras 102 operating with the processing platform are configured to detect pose of markers, e.g., reflective markers, on instruments, the patient (e.g., Dynamic Reference Base (DRB)), a surgical robot, etc.

Instruments

Navigated Instruments

The ExcelsiusHub works with all preexisting Globus navigated, arrayed instrumentation. This includes the drills, awls, probes, taps, and drivers for placement of Globus Screws and the dilators, disc preparation instruments (curettes, Cobb elevators, rasps, scrapers, etc.), trials, and inserters for navigated placement of Globus Interbodies. Each instrument is identified by a unique array pattern that is recognized by the camera.

Patient Attachment and Registration Instruments

The ExcelsiusHub may be used with existing patient fixation instruments and the current DRB.

Registration Fixtures

The ExcelsiusHub may be used with existing intra-op registration fixtures and the fluoroscopy registration.

System Software

The software operating with the ExcelsiusHub may include existing Spine software available on the ExcelsiusGPS Robotic System. The system software may be responsible for all navigation functions, data storage, network connectivity, user management, case management, and safety functions.

Applications

Spine surgical procedures are supported by the ExcelsiusHub System. The CONFIGURE tab displays procedure types. The spine procedural steps are the same as seen on ExcelsiusGPS Robotic System as the software is the same on both pieces of hardware.

Spine Procedures

Various Spinal surgical procedures Spinal surgical procedures supported by the ExcelsiusHub System are listed in the table below.

| Supported Spine Procedures | |
|---|---|
| Procedures | Patient Position |
| Posterior Cervical | Prone |
| Posterior Thoracic | Prone |
| Anterolateral Thoracic | Lateral |
| Posterior Lumbar | Prone |
| Lateral Lumbar | Lateral |
| Lateral Lumbar Interbody Fusion | Lateral |
| Transforaminal Lumbar Interbody Fusion | Prone |
| Posterior Lumbar Interbody Fusion | Prone |

Globus spinal implant systems that are compatible with the ExcelsiusHub System include those listed in the table below.

| Compatible Spinal Implant Systems |
|---|
| CREO Stabilization System |
| REVERE Stabilization System |
| REVOLVE Stabilization System |
| ELLIPSE Occipito-Cervico-Throacic Spinal System |
| QUARTEX Occipito-Cervico-Throacic Spinal System |
| SUSTAIN Spacers (Oblique, Small) (Posterior Interbody) |
| ALTERA Expandable Spacers (Posterior Interbody) |
| RISE Expandable Spacers (Posterior Interbody) |
| CALIBER Expandable Spacers (Posterior Interbody) |
| RISE-L Spacers (Lateral Interbody) |
| CALIBER-L Expandable Spacers (Lateral Interbody) |
| ELSA Integrated Expandable Spacers (Lateral Interbody) |

Procedure Setup

Configure Tab

Figure 2:
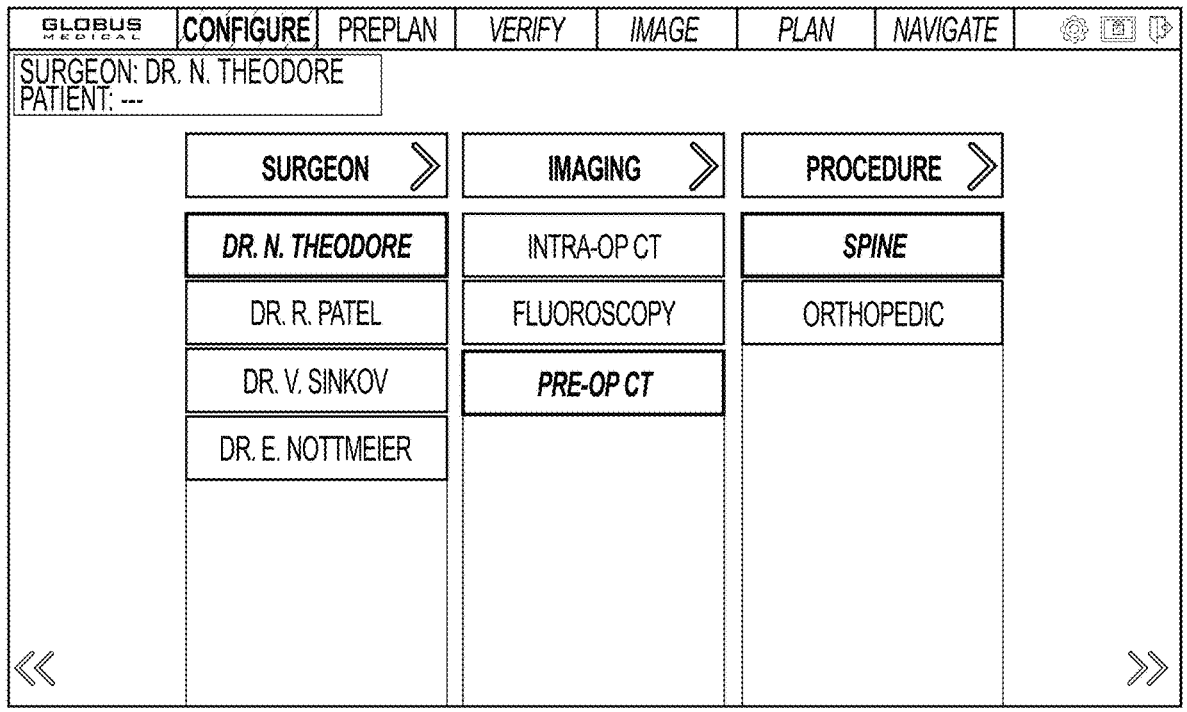
FIG. 2 illustrates an example user interface of the CONFIGURE tab during Procedure Setup according to some embodiments.

After selecting a case, the CONFIGURE tab is displayed on the monitor. An example user interface is shown in FIG. 2 according to some embodiments. Using the CONFIGURE tab select the surgeon from among a list of registered surgeons, the imaging modality and the procedure type. The imaging modality can include intra-operative CT, fluoroscopy, and pre-operative CT. Click the right arrows to advance to the next tab.

Workflow Tab

Figure 3:
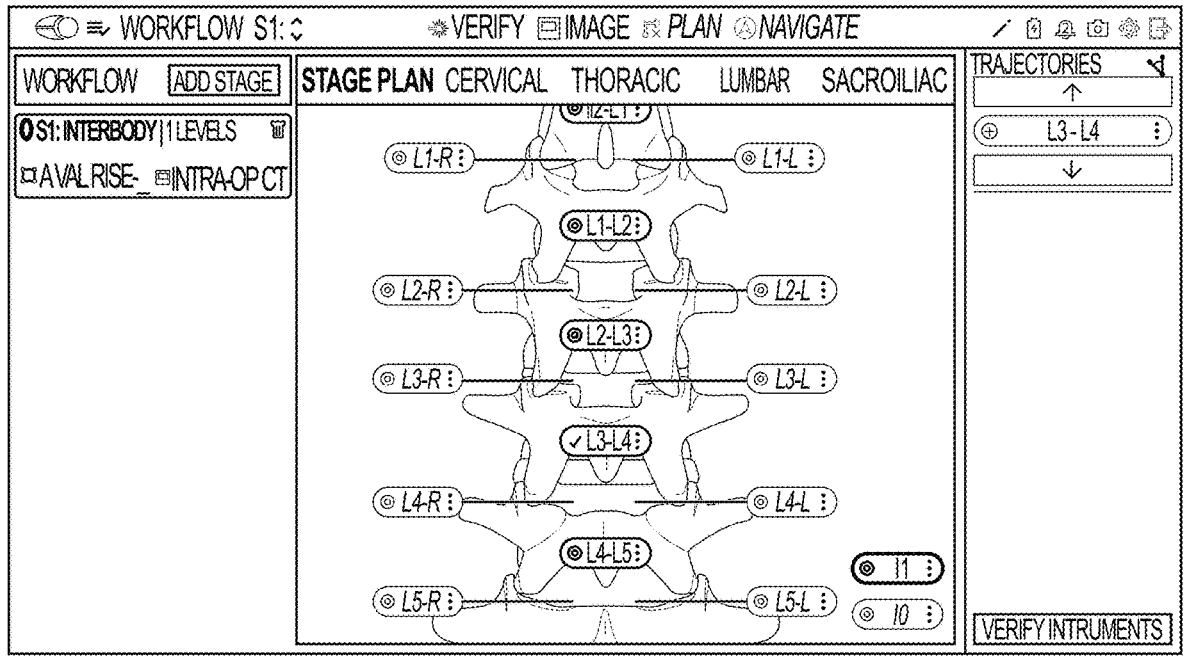
FIG. 3 illustrates an example user interface of the WORKFLOW tab during Procedure Setup according to some embodiments.

Using the WORKFLOW tab, select the desired stage of the procedure (e.g., interbody, or screws) in the desired order of operation (e.g., interbody first). For each stage, select the imaging modality, interbody implant system, and desired interbody level on the anatomical model, which may include cervical, thoracic, lumbar, and sacroiliac. Add stages to the workflow by clicking the "Add Stage" button. Click "Verify Instruments" to proceed to advance to the next tab. An example user interface is shown in FIG. 3 according to some embodiments.

Verify Tab

The VERIFY tab displays navigation details including visibility, location and verification status of the instruments selected on the WORKFLOW tab. Verification is used to indicate whether one or more instruments may be damaged, e.g., during handling. All instruments with arrays should be verified prior to use, either with a verification adapter, instrument, implant, or dilator, as appropriate.

Figure 4:
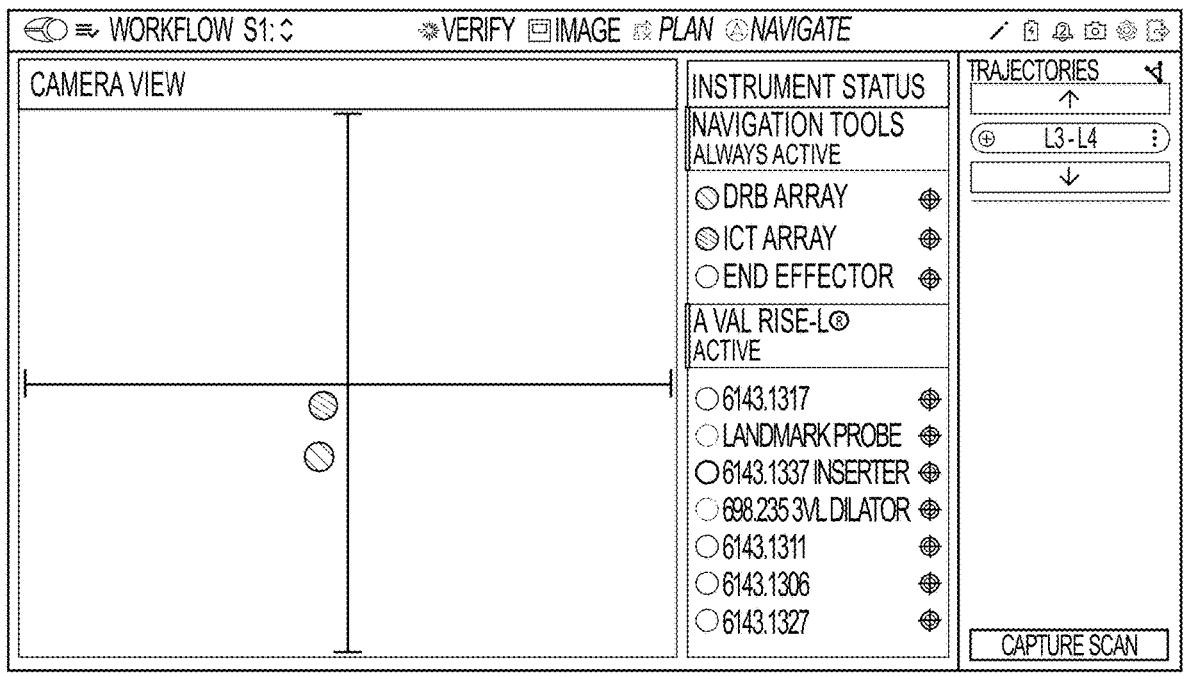
FIG. 4 illustrates an example user interface of the VERIFY tab during Procedure Setup according to some embodiments.

An example user interface is shown in FIG. 4 according to some embodiments. The VERIFY tab shows CAMERA VIEW and INSTRUMENT STATUS listing a set of identified instruments.

CAMERA VIEW can be operationally updated in real-time from the perspective of the camera with, e.g., color circles being displayed indicating instrument location. A solid colored circle can displayed to indicate that the corresponding instrument is visible to the cameras 102, while a hollow circle indicates that it is not visible to the cameras 102. Size of the colored circle can be dynamically updated to change size to indicate distance from the physical cameras 102. In one embodiment, the circle size is adapted to grow larger as the instrument is moved closer to the cameras 102 and smaller as the instrument is moved away from the cameras 102. An ideal distance from the cameras 102 may be approximately 2 meters or 6 feet, in accordance with some embodiments.

INSTRUMENT STATUS lists each instrument and its verification status, with corresponding color circles to identify each instrument. Verification status symbols are shown in FIG. 4, in accordance with some embodiments.

Instrument Verification

Figure 5:
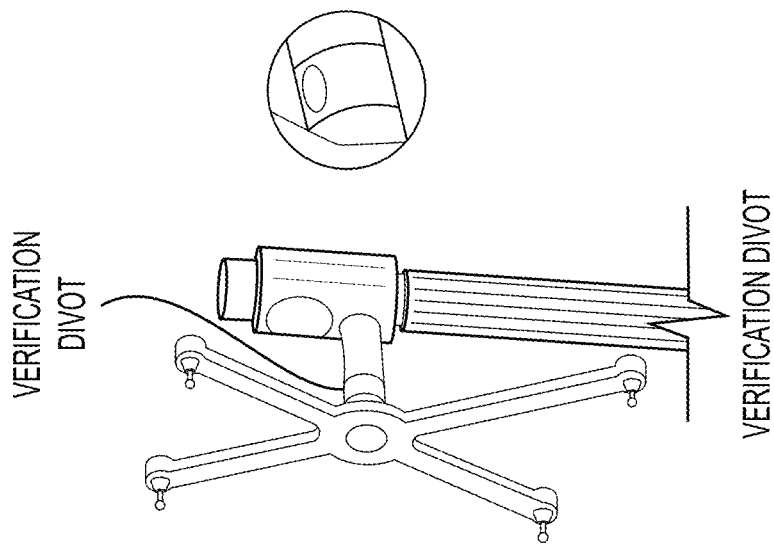
FIG. 5 illustrates an instrument verification using a verification divot according to some embodiments.
Figure 5:
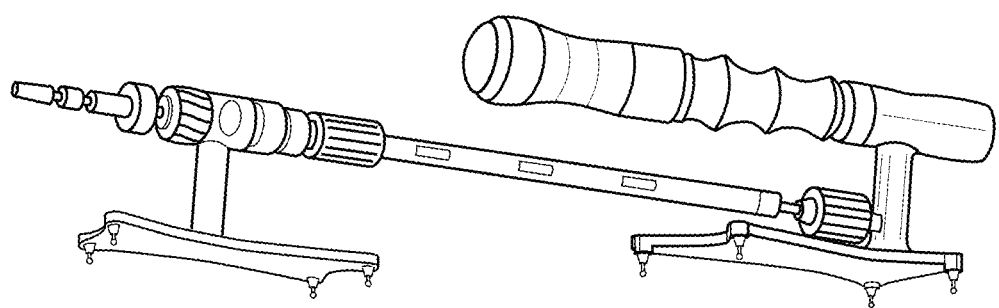

With reference to FIG. 5, each instrument can be verified by placing the tip of the instrument into a verification dot provided at a known location on another piece of equipment, e.g., on a registered instruments array or on a registered robot art of a surgical robot system, or by placing a verification adapter to be verified into a verification divot provided at a known location on the instrument, according to some embodiments. Divots can be formed at defined locations on navigated instrument arrays for use in verifying the instruments. If using a ExcelsiusGPS Robotic System, a divot can also be located on the top surface of the End Effector or other known location which can be tracked by the cameras 102. Next, ensure both instruments are visible to the cameras 102 and held steady. A pop-up screen then is displayed on the VERIFY tab to indicate operations of the verification progress.

Figure 6:
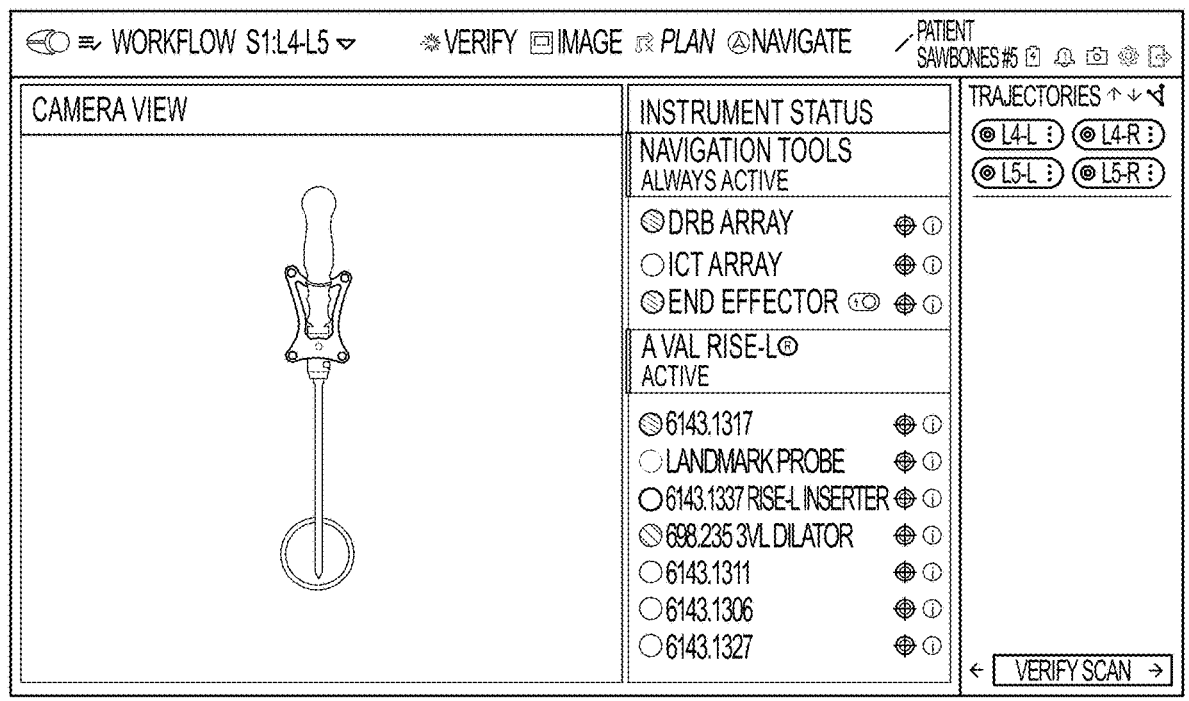
FIG. 6 illustrates an example user interface during instrument verification according to some embodiments.
Figure 6:
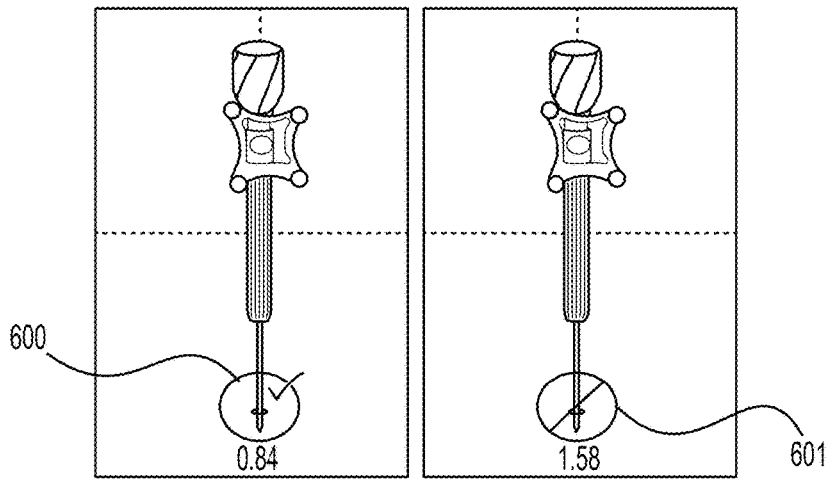

As shown in FIG. 6, once verification is complete, verification status is indicated on the screen with the tip error displayed in mm, according to some embodiments. If verification has failed a corresponding indication 600 is displayed, e.g., a red crossed circle is displayed and verification operations can be repeated until verification is completed successfully. In contrast, successful verification is indicated by another displayed indication 601, e.g., a green circle. When all instruments are successfully verified, the user can click the right arrow to advance to the next tab.

Patient Attachment Instruments

Patient attachment instruments are secured to rigid bony anatomy neighboring the surgical site. A user selects the desired instrument. Patient attachment instruments should be placed no more than 185 mm from the center of the surgical site to maintain accuracy, in accordance with some embodiments. Bone clamps are clamped onto anatomical structures such as the spinous process, iliac crest, long bone, or any rigid bony structure that can be safely clamped. Quattro spikes are inserted into the iliac crest or a long bone. Rod attachments are secured to an existing spinal rod, e.g., 4.5 mm to 6.35 mm in diameter. Example recommended anatomic locations for the various patient attachment instruments are described in the table below according to some embodiments.

| Patient Attachment Instruments - Recommended Anatomic Locations | | | |
|---|---|---|---|
| Spine Procedures | Patient Position | Patient Attachment Instrument | Recommended Patient Attachment Instrument Location |
| Posterior Cervical | Prone | Bone Clamp | Spinous Process C2-T3 |
| | | Rod Attachment | Existing Rod |
| Posterior Thoracic | Prone | Bone Clamp | Spinous Process T1-L1 |
| | | Rod Attachment | Existing Rod |
| Anterolateral Thoracic | Lateral | Bone Clamp | Spinous Process T1-L1 |
| Posterior Lumbar | Prone | Quattro Spike | Iliac Crest |
| | | Low Profile Quattro Spike | Iliac Crest |
| | | Bone Clamp | Spinous Process T12-L5 |
| | | Rod Attachment | Existing Rod |
| Lateral Lumbar | Lateral | Quattro Spike | Iliac Crest |
| | | Low Profile Quattro Spike | Iliac Crest |
| | | Bone Clamp | Spinous Process T12-L5 |
| | | Rod Attachment | Existing Rod |

Dynamic Reference Base Insertion

A user positions a compression clamp on the Dynamic Reference Base (DRB) over the patient attachment instrument and tightens the knob, as shown in FIG. 7 according to some embodiments. If needed, a clamp driver can be used to further tighten the DRB knob, as shown in FIG. 8 according to some embodiments. The user positions the reflective markers on the DRB in the direction of the cameras 102. Care should be taken with initial placement of the patient reference instrument as to not interfere with the surgical procedure. Following navigation, the patient attachment instrument is removed.

Surveillance Marker

A surveillance marker is inserted into rigid bony anatomy to enable the camera tracking system to use the cameras 102 to track the relative distance to the DRB, e.g., to identify unwanted shifts in the DRB during the procedure. FIG. 9 illustrates a placement of a DRB 900 spaced apart from a surveillance marker 902 according to some embodiments.

Surveillance markers may be inserted into the iliac crest or long bone, or may be attached to the spinous process using a bone clamp. The user verifies that the clamp is rigidly secured. The surveillance marker should be placed no more than 185 mm from the Dynamic Reference Base in some embodiments. Example recommended anatomic locations for the various surveillance markers are described in the table below, according to some embodiments.

| Surveillance Marker - Recommended Anatomic Locations | | | |
|---|---|---|---|
| Procedures | Patient Position | Marker | Recommended Surveillance Marker Location |
| Posterior Cervical | Prone | On Bone Clamp | Spinous Process C2-T3 |
| Posterior Thoracic | Prone | Single | Iliac Crest |
| | | On Bone Clamp | Spinous Process T1-L1 |
| Anterolateral Thoracic | Lateral | On Bone Clamp | Spinous Process T1-L1 |
| Posterior Lumbar | Prone | Single | Iliac Crest |
| | | On Bone Clamp | Spinous Process T12-L5 |
| Lateral Lumbar | Lateral | Single | Iliac Crest |
| | | On Bone Clamp | Spinous Process T12-L5 |

The user attaches a disposable reflective marker to the marker post of the surveillance marker 902. [0082] The user attaches the impaction cap, designed to fit over the reflective marker sphere 904, onto the surveillance marker 902. The user inserts the surveillance marker 902 into rigid bony anatomy near the surgical site, and may gently impact with a mallet. The user removes the impaction cap. The user removes the reflective marker 904 prior to using the removal tool. To use a bone clamp with the marker, the user attaches a disposable marker onto the tip of the bone clamp. The user may use the clamp driver to secure the bone clamp. The user then verifies that the clamp is rigidly secured.

Removal

The quattro spikes and surveillance marker are removed from bony anatomy manually or using the removal tool. The bone clamp is removed by loosening the clamp with the clamp driver, attaching the removal tool and lifting up the bone clamp, as shown in FIG. 10 according to some embodiments.

Intra-Operative Ct Imaging Workflow
Intra-Op Ct Registration Fixture Setup

Figure 11:
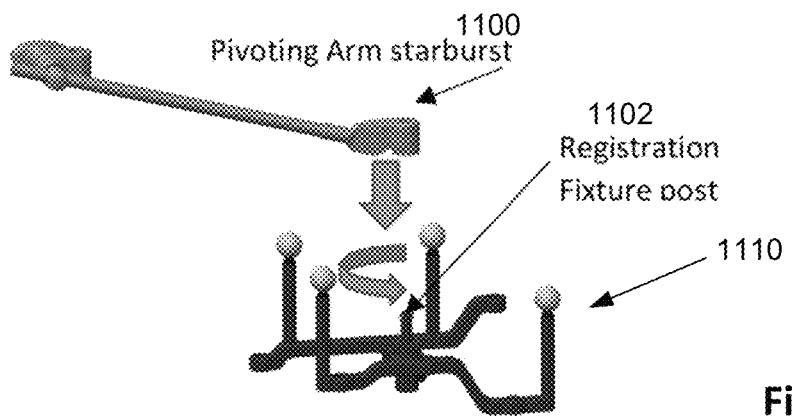
FIG. 11 illustrates a process for securing a pivoting arm starburst on a registration fixture according to some embodiments.
Figure 12:
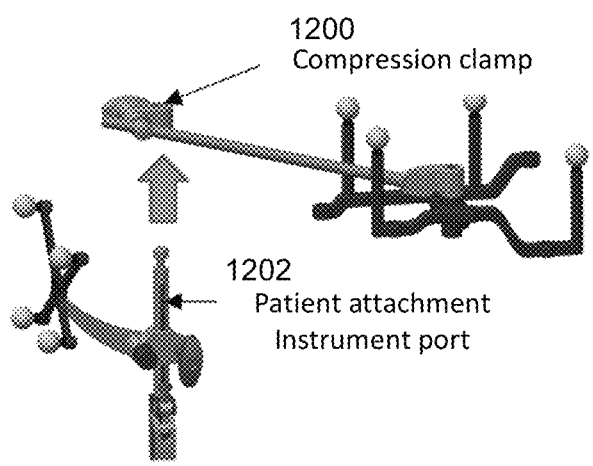
FIG. 12 illustrates a process for securing a registration fixture to a patient attachment instrument post according to some embodiments.
Figure 13:
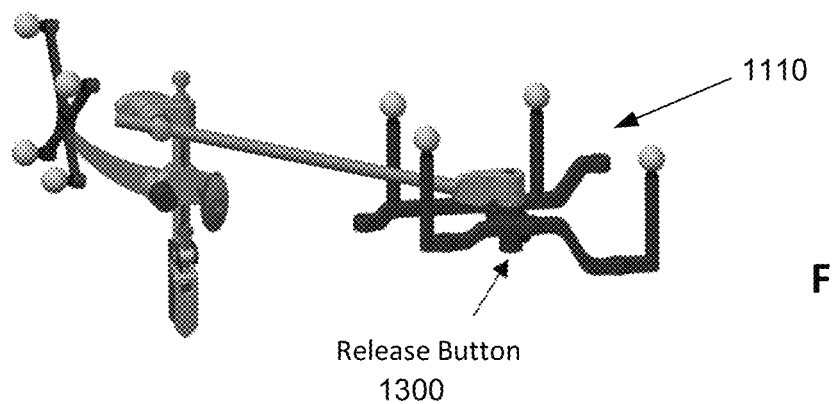
FIG. 13 illustrates a complete intra-op CT registration assembly and release button according to some embodiments.

A pivoting arm starburst 1100 is placed over a starburst post of the registration fixture post 1102 of a registration fixture 1110 and rotated 90° to secure, as shown in FIG. 11 according to some embodiments. The registration fixture 1110 is positioned on a patient attachment instrument post 1202 and a compression clamp 1200 knob is tightened, as shown in FIG. 12 according to some embodiments. If needed, a clamp driver can be used to further tighten the knob on the compression clamp 1200. The completed assembly is shown in FIG. 13 according to some embodiments. To release the pivoting arm, a release button 1300 on the fixture is pushed, the pivoting arm 90° is rotated and pull up. The intra-op CT registration fixture has six degrees of freedom and can be moved by adjusting one of the three joints so that it is stable and hovering over the surgical site. Only the metal fiducials embedded in the fixture need to be in the 3D scan (not the reflective markers). It may be operationally helpful or necessary for the intra-op CT registration fixture to not move between image acquisition and performing an anatomical landmark check.

Loading the Image

Figure 14:
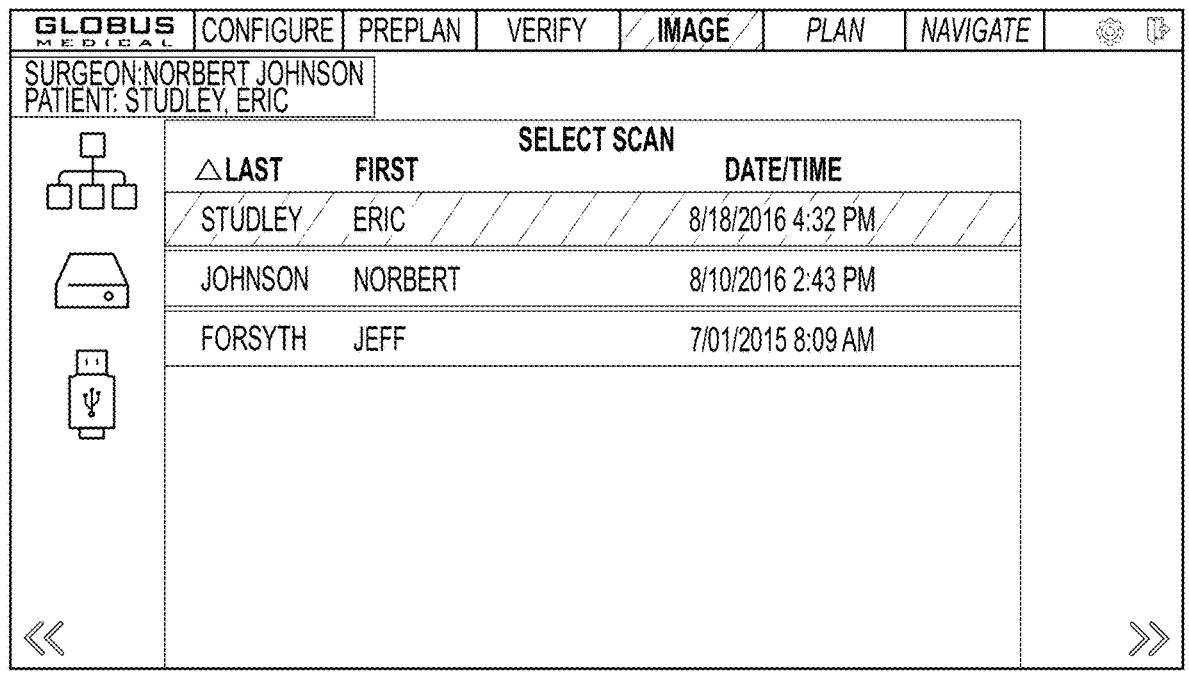
FIG. 14 illustrates an example user interface of the IMAGE tab during an intra-operative CT imaging workflow according to some embodiments.

Selection of the IMAGE tab shown in FIG. 14 displays the steps needed to load a CT scan image according to some embodiments. The image can be loaded from, e.g., a USB drive, hard drive, and/or a networked device. If the image is transferred via the Ethernet, it may automatically appear on the hard drive when the transfer is complete.

To view images on a USB drive, the USB drive is inserted into a USB port on the connector panel 107. To trigger loading of an image, the hard drive or USB drive icon can be selected followed by selection of the desired patient image. The right arrows can be selected to load the patient images and advance to the next tab.

Manual Registration

Figure 15:
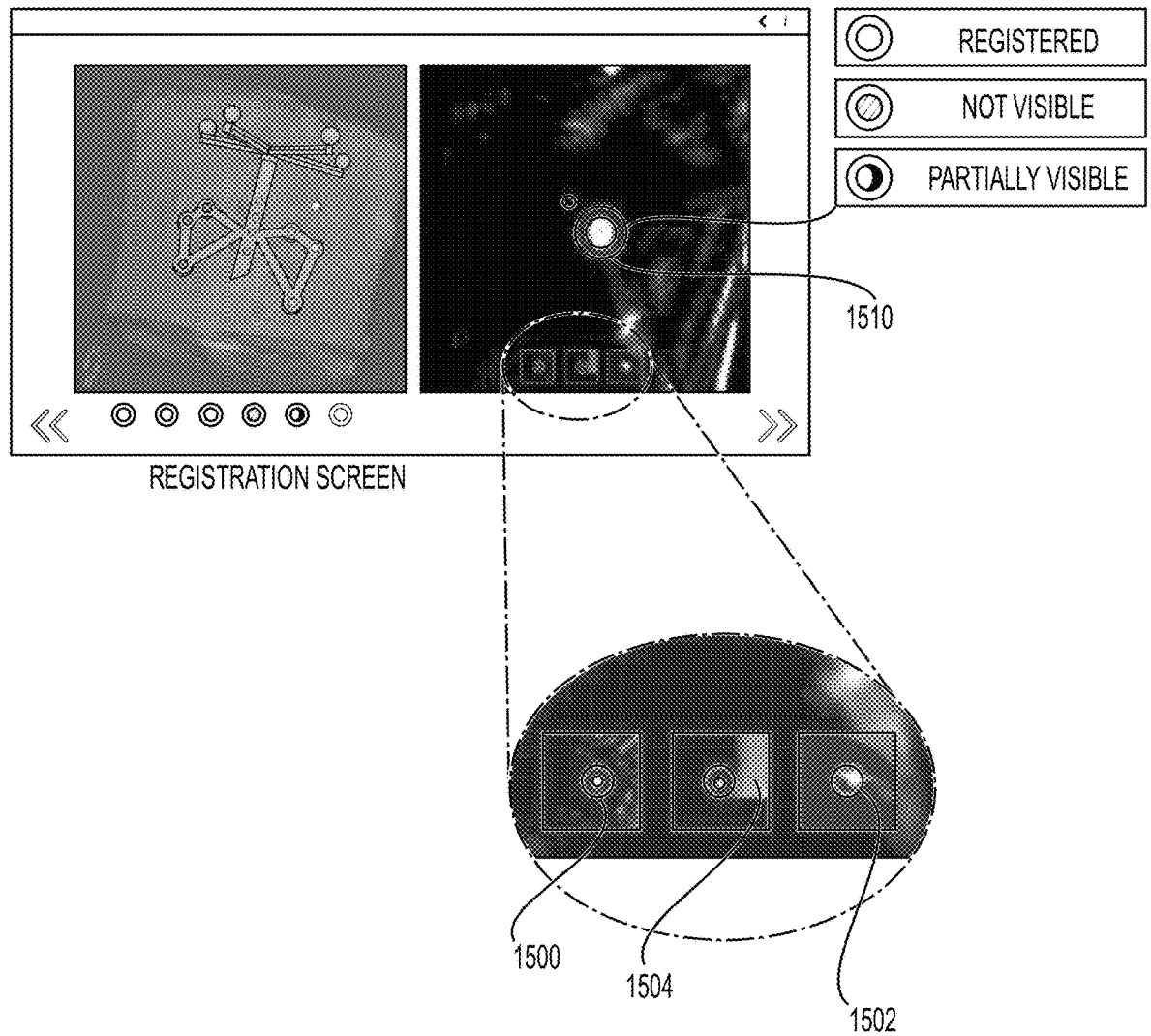
FIG. 15 illustrates an example user interface of the manual registration screen during an intra-operative CT imaging workflow according to some embodiments.

Automatic registration can be performed when loading images. However, if automatic registrations operations fail or otherwise not utilized, then a manual registration screen can be displayed to allow manual registration as shown in FIG. 15 according to some embodiments. The image on the left panel of the registration screen is a full scan with a depiction of the intra-operative CT.

A registration fixture and seven fiducials, in some embodiments of the fixture, should be visible below the image. Fiducials that are not registered need to be adjusted by the operator. On the screen, a fiducial is selected which is not yet registered; causing that image to then appear on the right. A colored circle 1500 is moved on the screen by a user until the user determines that it surrounds a displayed fiducial marker. The three small boxes 1510 shown in FIG. 15 at the bottom of the right panel show the x, y and z direction of the fiducial and all should be adjusted until the blue circle is centered. In the example embodiment of FIG. 15, a registered fiducial 1500 is displayed with a solid color filled-in center, another fiducial 1504 which is not visible to the system is displayed with a non-filled-in center, and yet another fiducial 1502 which is partially visible to the system is displayed with a partially filled-in center.

Ensure that all seven fiducials are properly identified by viewing the 3D model of the intra-op registration fixture. A fiducial may be deleted by selecting the delete icon on the right panel. Click the right arrows to confirm that the fiducials have been properly identified before proceeding to the next step.

Figure 31:
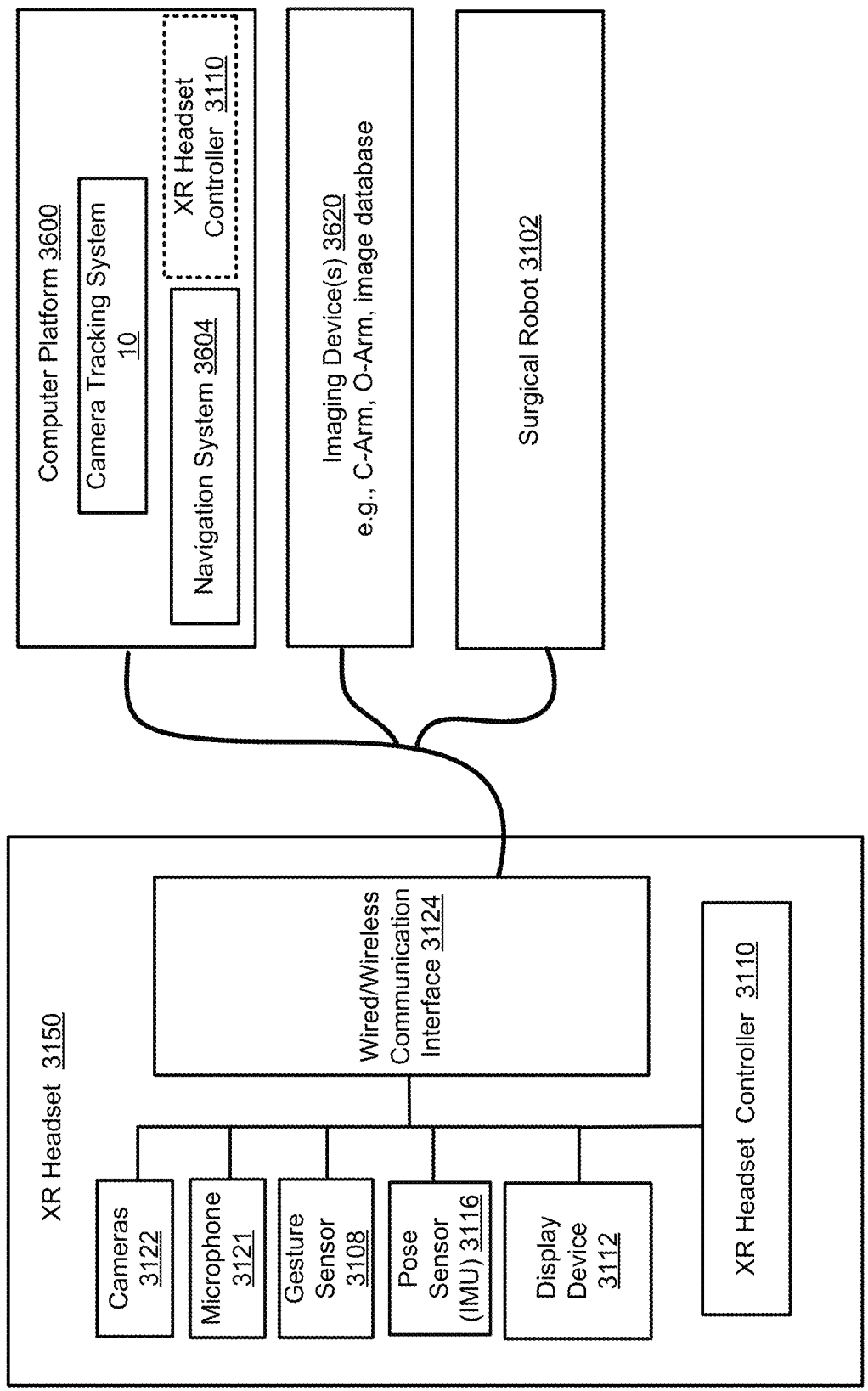
FIG. 31 illustrates a block diagram of surgical system which includes a camera tracking system and navigation system, and further optionally includes a surgical robot and XR headset, which are each operative in accordance with some embodiments.
Figure 32:
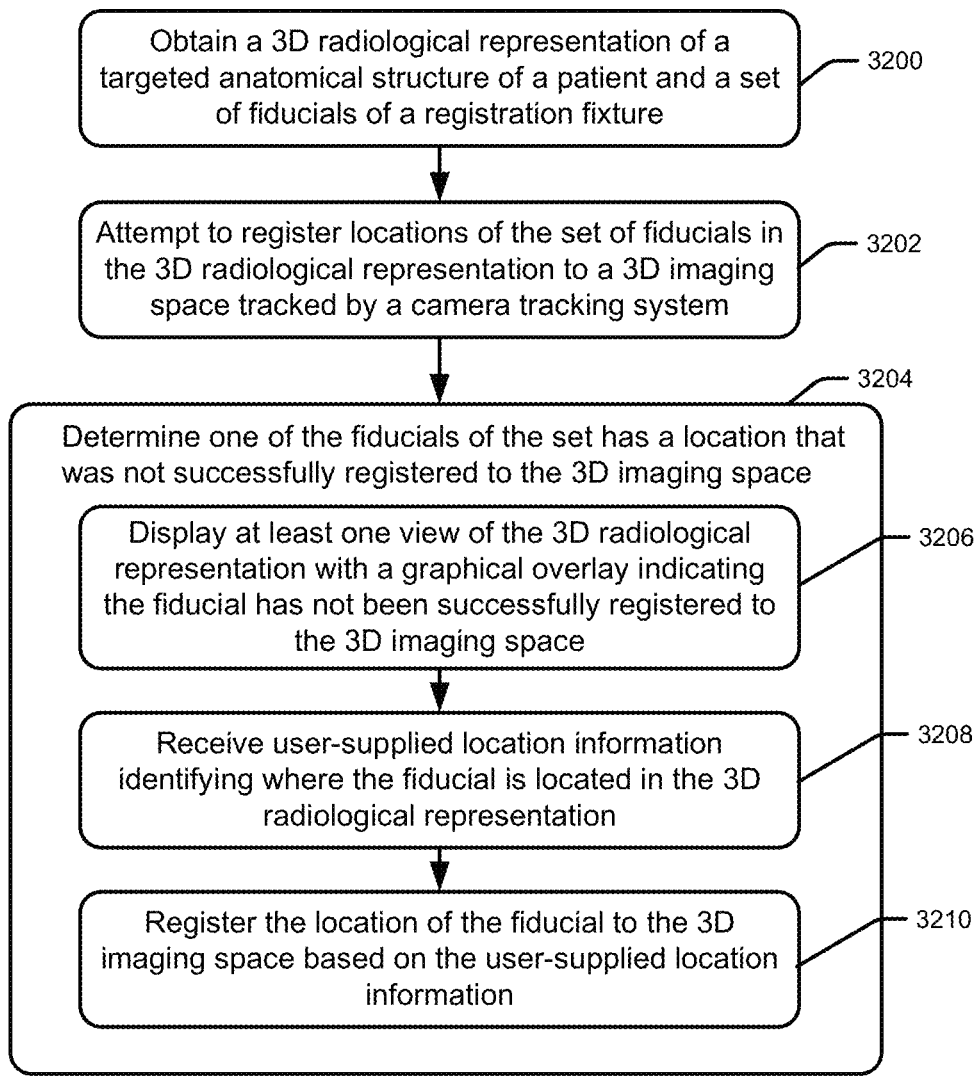
FIGS. 32-34 illustrate operations that may be performed by a surgical system in accordance with some embodiments.

Corresponding operations that may be performed are now described in the context of FIG. 32. FIG. 32 illustrates operations that may be performed by a surgical system in accordance with some embodiments. The surgical system includes at least one processor that may reside in a component of the computer platform 3600, such as the camera tracking system 10 and/or the navigation system 3604. Referring to FIG. 32, the operations include to obtain 3200 a three-dimensional (3D) radiological representation, e.g., CT scan(s) and/or fluoroscopy scan(s), of a targeted anatomical structure of a patient and a set of fiducials of a registration fixture, e.g., 900 in FIGS. 9 and/or 2100 in FIG. 21. The operations attempt 3202 to register locations of the set of fiducials in the 3D radiological representation to a 3D imaging space tracked by a camera tracking system, e.g., system 10 in FIG. 31. The registration may include attempting to correlate the pose (e.g., location and orientation) set of fiducials in the 3D radiological representation to the pose of optical markers detected in the 3D imaging space. Based on determining 3204 one of the fiducials of the set has a location that was not successfully registered to the 3D imaging space, the operations display 3206 at least one view of the 3D radiological representation with a graphical overlay indicating the fiducial has not been successfully registered to the 3D imaging space, receive 3208 user-supplied location information identifying where the fiducial is located in the 3D radiological representation, and register 3210 the location of the fiducial to the 3D imaging space based on the user-supplied location information.

The operation to receive 3208 user-supplied location information identifying where the fiducial is located in the 3D radiological representation, may include to display three orthogonal views of the fiducial in the 3D radiological representation and/or the 3D imaging space, and display a graphical object overlaid on an initial location in the three orthogonal views. The operation moves location of where the graphical object is displayed in the three orthogonal views responsive to input from the user through a user interface, and determine location of the fiducial in the 3D radiological representation and/or the 3D imaging space based on the location of where the graphical object is displayed in the three orthogonal views. The operation registers the location of the fiducial to the 3D imaging space is based on the determined location of the fiducial in the 3D radiological representation.

The operation to receive 3208 may display the graphical object overlaid on the initial location in the three orthogonal views, may include to determine the initial location to correspond to a predicted location of the fiducial based on relative locations of fiducials defined by a registration fixture template.

The operation to receive 3208 may further include to move the location where the graphical object is displayed in the three orthogonal views to track directional inputs received through the user interface of the surgical system.

The operation to attempt 3202 to register locations of the set of fiducials in the 3D radiological representation to the 3D imaging space tracked by the camera tracking system, may include to obtain, from at least one camera of the camera tracking system, an optical image of a reference array fixated to the patient. The reference array including a set of optical markers detectable by the at least one camera of the camera tracking system in the 3D imaging space. The reference array may also be connected to the registration fixture. The operation may then attempt to register locations of a pattern of the set of optical markers to locations of a pattern of the set of fiducials in the 3D radiological representation, and identify any of the optical markers of the reference array that are not successfully registered to any of the fiducials of the registration fixture.

Landmark Check

After registration has been completed, a landmark check can be performed to ensure that the registration was calculated successfully. Using the verification probe, an anatomical landmark or a fiducial is touched on the registration fixture to trigger verification that the corresponding location is shown on the system monitor. This process can be repeated using other, e.g., 2 to 3 other landmarks.

Corresponding operations that may be performed by the surgical system may include to track locations of a tool captured in video from a camera of the camera tracking system while the tool is being moved by a user toward one of the fiducials that was successfully registered to the 3D image space, and display updated representations of the tool according to the tracked locations in the 3D imaging space. The operations confirm registration accuracy of the one of the fiducials that was successfully registered to the 3D image space based on comparison of a designated one of the tracked locations of the tool to the location of the one of the fiducials registered to the 3D image space.

Removing Registration Fixture

The Intra-op CT Registration Fixture can then be removed while ensuring the patient attachment instrument does not move.

PLAN Tab

Figure 16:
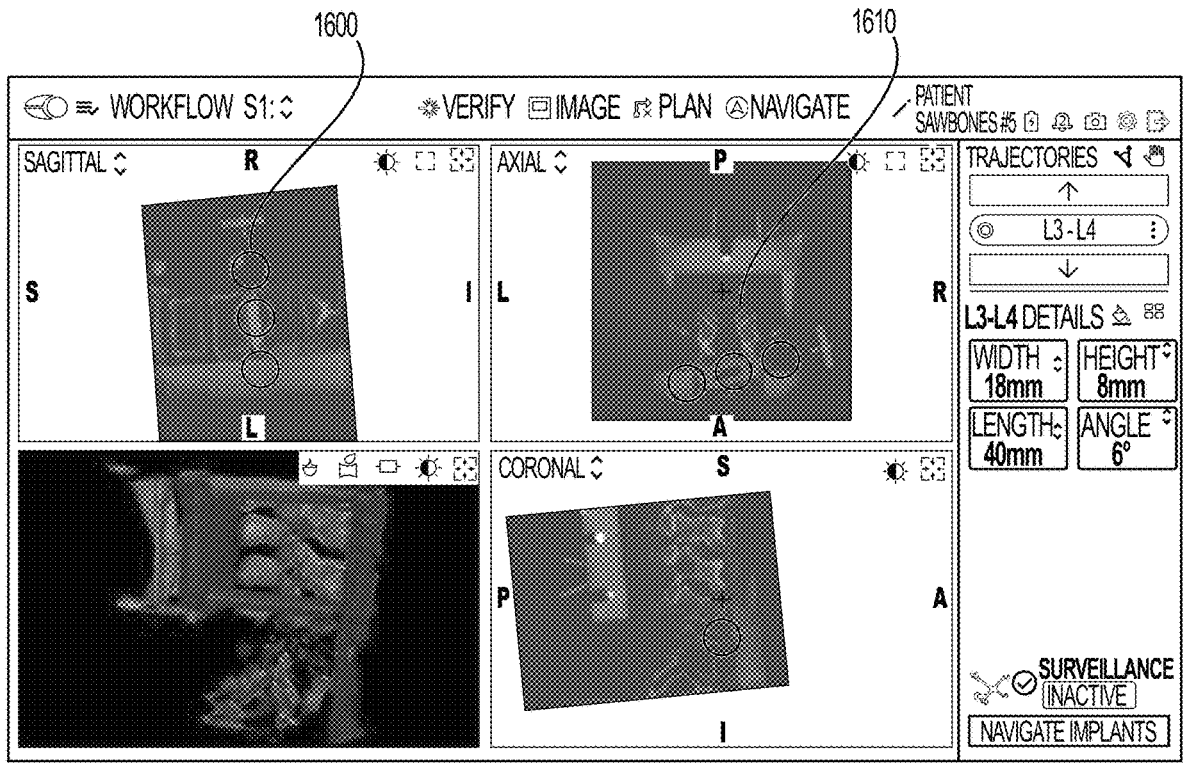
FIG. 16 illustrates an example user interface of the PLAN tab during an intra-operative CT imaging workflow according to some embodiments.

The PLAN tab allows the user to plan all screw insertion trajectories (e.g., 1600) and interbody placement (e.g., 1610) on the patient image, such as shown in the example user interface of FIG. 16 according to some embodiments. Implants are preloaded (e.g., with defined characteristics) in the system and displayed on the right-hand side of the screen, based on selections made in the PREPLAN tab.

To add an implant onto the planning page, a user can drag and drop the appropriate implant label on the image at the desired slice. The active plan is shown in a defined color. Details of the active screw plan are shown on the lower right of the screen, including screw family, diameter, and length. The right arrow can be selected to advance to the next tab once plans are complete for all screws.

Once the implant is dropped on the image, the implant planning features are used to adjust implant location by, e.g., dragging the implant image on the touch screen. The user selects or otherwise defines the specific implant size (width, length, height, lordosis) on the right panel of the screen.

Figure 33:
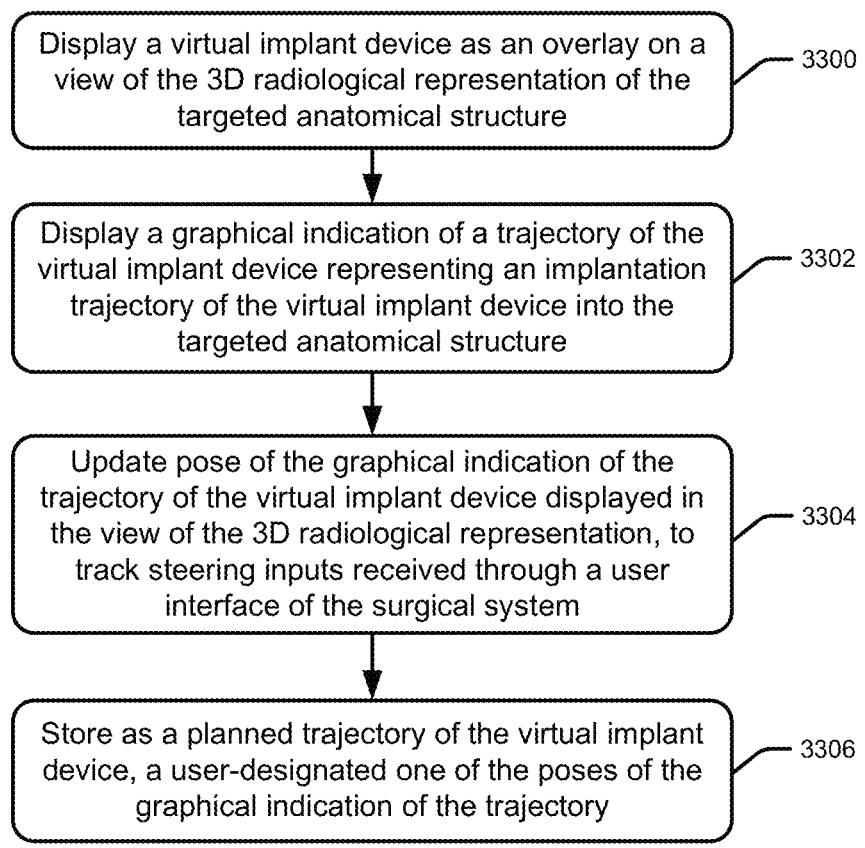

Corresponding operations that may be performed are now described in the context of FIG. 33. FIG. 33 illustrates operations that may be performed by the surgical system in accordance with some embodiments. Referring to FIG. 33, the operations include to display 3300 a virtual implant device as an overlay on a view of the 3D radiological representation of the targeted anatomical structure, and display 3302 a graphical indication of a trajectory of the virtual implant device representing an implantation trajectory of the virtual implant device into the targeted anatomical structure. The operations update 3304 pose of the graphical indication of the trajectory of the virtual implant device displayed in the view of the 3D radiological representation, to track steering inputs received through a user interface of the surgical system. The operations store 3306 as a planned trajectory of the virtual implant device, a user-designated one of the poses of the graphical indication of the trajectory.

The operations may further include to display a set of implant devices which are selectable by a user for implant planning, and generate a graphical representation of the virtual implant device based on a template of one of the set of user-selectable implant devices which is selected by a user through the user interface.

NAVIGATE Tab

Figure 17:
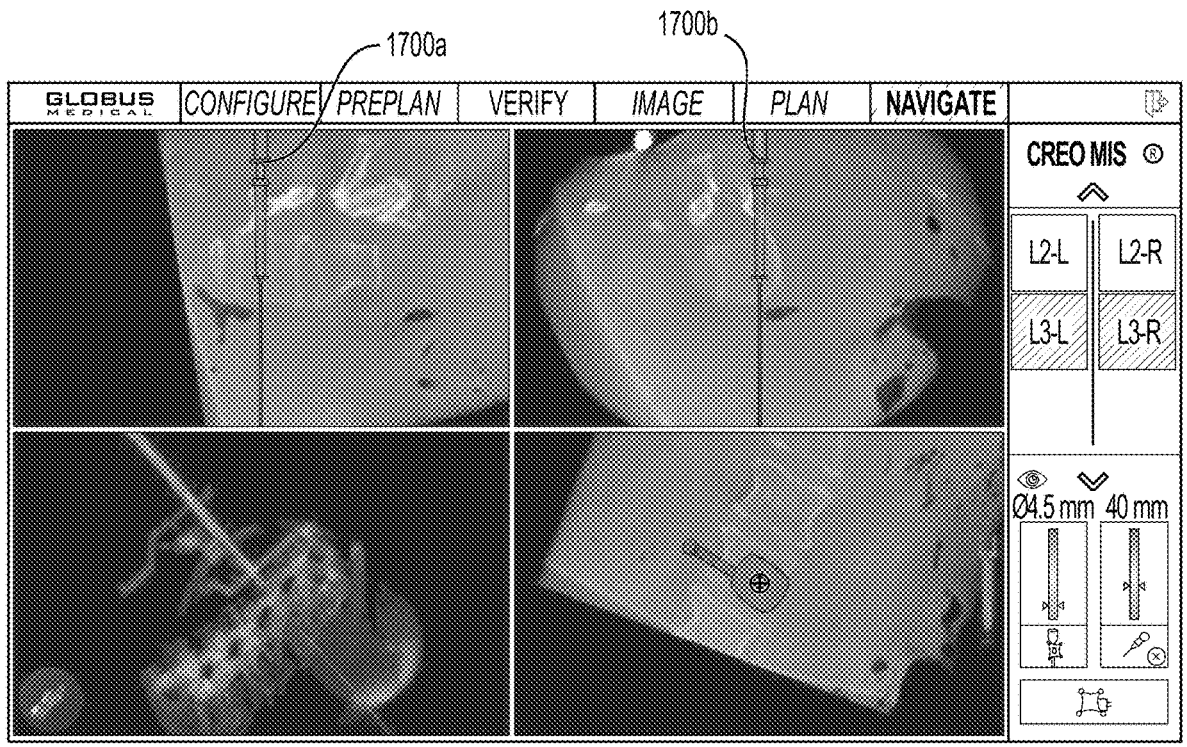
FIG. 17 illustrates an example user interface of the NAVIGATE tab during an intra-operative CT imaging workflow according to some embodiments.

The NAVIGATE tab allows the user to visualize the navigated instrument trajectory and the planned trajectory with respect to patient anatomy. An example user interface is shown in FIG. 17 according to some embodiments. The desired implant label can be selected on the right of the screen.

The real-time instrument/implant trajectory 1700*a*, 1700*b* (actual plan) is displayed on the patient images, e.g., in orthogonal image slice views, along with the planned screw, allowing the user to confirm the desired trajectory. If the real-time trajectory is not acceptable, the user can return to the PLAN tab to select another trajectory. If the real-time trajectory is acceptable, the user inserts the screw according to the instrument's current trajectory to the desired depth.

Navigated instruments are displayed as they are advanced to the planned position. While navigating the instruments, the user repetitively observes the monitor and surgical site to ensure consistency between tactile and navigation feedback.

Corresponding operations by the surgical system may include to display the planned trajectory of virtual implant device as an overlay on the view of the 3D radiological representation of the targeted anatomical structure. The operations obtain, from at least one camera of the camera tracking system, optical images of a reference array fixated to a real-implant device corresponding to the virtual implant device, the reference array including a set of optical markers detectable by the at least one camera of the camera tracking system in the 3D imaging space. The operations track pose of the real-implant device in the 3D imaging space based on pose of the reference array in the optical images while the real implant device is being positioned by a user relative to the targeted anatomical structure of the patient. The operations display updated graphical representations of the real-implant device relative to the planned trajectory of the virtual implant device according to the tracked pose in the 3D imaging space.

Pre-Operative Ct Imaging Workflow

IMAGE Tab

Loading the Image

Figure 18:
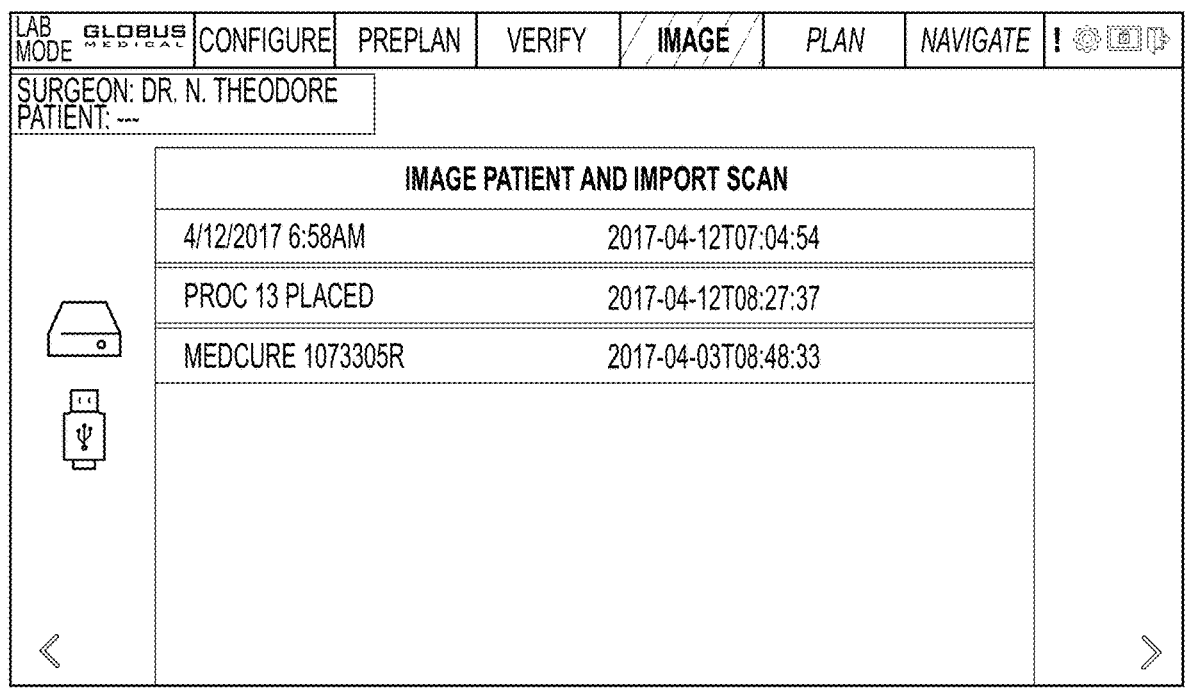
FIG. 18 illustrates an example user interface of the IMAGE tab during a pre-operative CT imaging workflow according to some embodiments.

The IMAGE tab shows the steps needed to load a CT scan image. An example user interface is shown in FIG. 18 according to some embodiments. The image can be loaded from, e.g., a USB drive, hard drive, or networked device. If the image is transferred through the Ethernet, it may automatically appear on the hard drive when the transfer is complete.

To view images on a USB drive, the USB drive is inserted into the USB port on the connector panel. To load an image, the user selects the hard drive or USB drive icon and selects the desired patient image. The right arrows can be selected to load the patient images and advance to the next tab.

PLAN Tab

Figure 19:
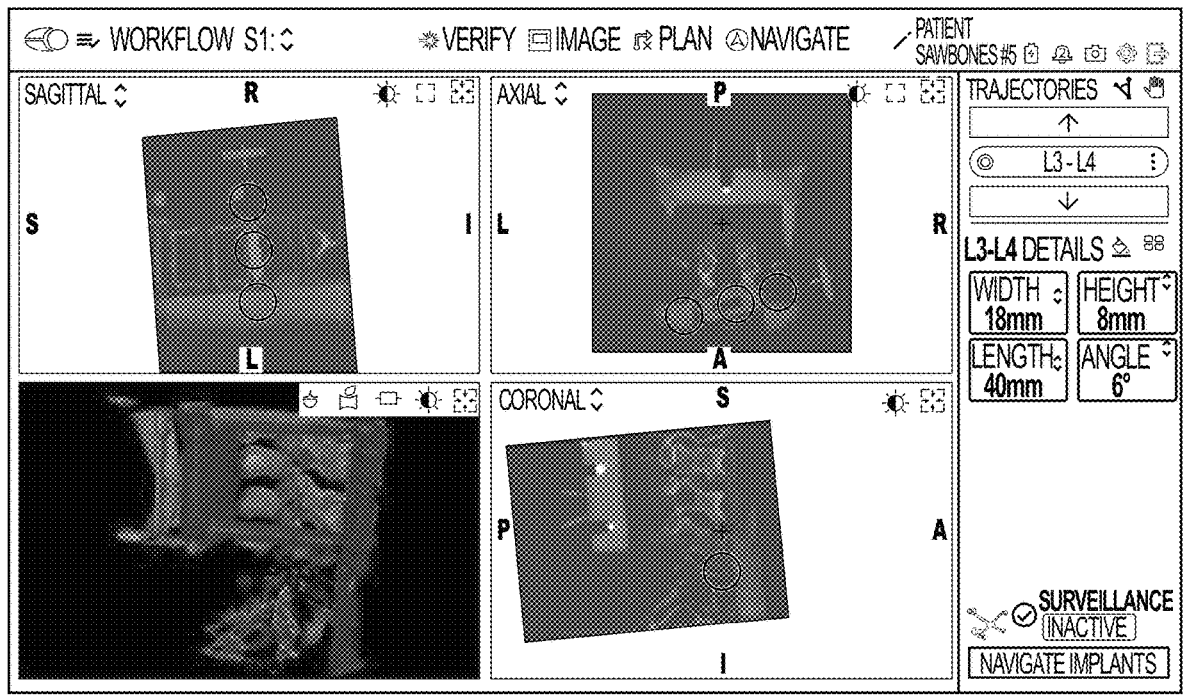
FIG. 19 illustrates an example user interface of the PLAN tab during a pre-operative CT imaging workflow according to some embodiments.

The PLAN tab allows the user to plan all screw trajectories and interbody placement on the patient image. An example user interface is shown in FIG. 19 according to some embodiments. Implants are preloaded (e.g., characteristics predefined in the system) on the right side of the screen, based on selections made in the PREPLAN tab.

To add an implant onto the planning page, a user may drag and drop the appropriate implant label on the image at the desired slice. The active plan is shown in a defined color. Details of the active screw plan are shown on the lower right of the screen, including screw family, diameter, and length. The right arrows can be selected to advance to the next tab once plans are complete for all screws.

Once the implant is dropped on the image, the implant planning features a performed to adjust implant location by, e.g., dragging the implant image on the touch screen. The specific implant size (width, length, height, lordosis) is selected or defined on the right panel of the screen.

NAVIGATE Tab

The NAVIGATE tab allows the user to visualize the navigated instruments and trajectory alignment with respect to patient anatomy, according to the implant plan.

Registration Setup

Figure 20:
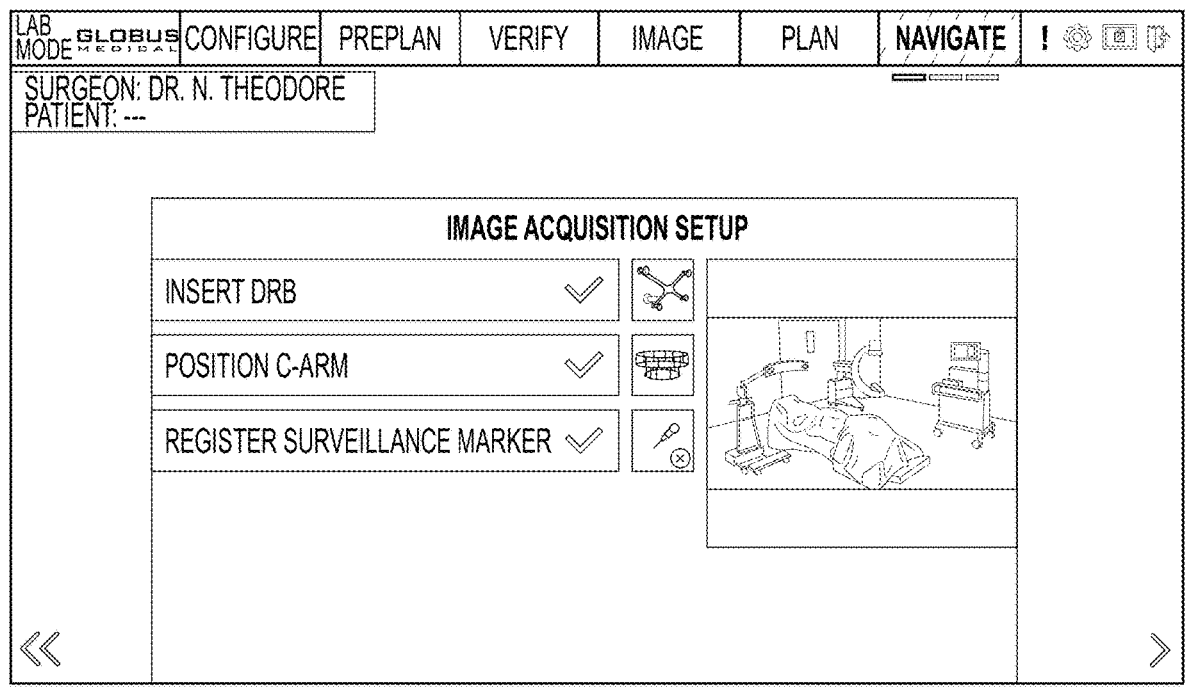
FIG. 20 illustrates an example user interface of the NAVIGATE tab during a pre-operative CT imaging workflow according to some embodiments.

Another display screen, e.g., as shown in FIG. 20, highlights the three steps to complete before the fluoroscopy images can be taken to register the pre-operative CT image, according to some embodiments. The steps may be to insert the DRB, position the C-ARM of an C-arm imaging device, and register a surveillance marker with the camera navigation system. Animation may be used to visually depict the steps.

Figure 21:
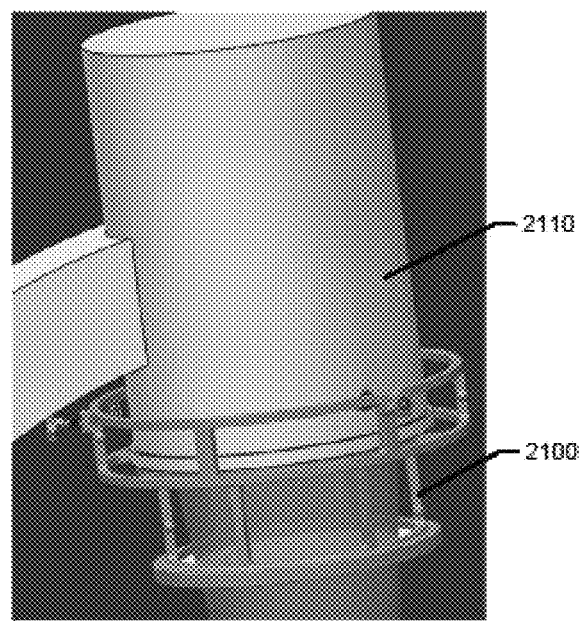
FIG. 21 illustrates a fluoroscopy registration fixture attached to an image intensifier according to some embodiments.

A Fluoroscopy Registration Fixture 2100 is attached to an image intensifier 2110 on the C-arm, as shown in FIG. 21 according to some embodiments, by turning the clamp clockwise until tight. New optical markers are installed on the fixture 2100 prior to orienting the fixture 2100 such that the optical markers are facing the cameras 102. A video capture cable is connected to the C-arm viewing station. A video capture USB cable is inserted into one of the USB ports on ExcelsiusHub connector panel 107.

The user may ensure that the Dynamic Reference Base is visible to the cameras 102 after the C-Arm is in place.

The surveillance marker is registered with the camera tracking system by, e.g., placing an instrument close to the reflective sphere 904 on the surveillance marker 902 but not touching. The box is then displayed in a defined color when it is activated.

The right arrows can be selected to advance to the next tab.

Registration

Operations acquire the intra-operative fluoroscopic images, one anteroposterior (AP) and one lateral for each level planned. The same image may be used for multiple levels.

In some embodiments, the operations verify that the following three conditions are met prior to enable acquisition of the images: 1) the DRB is visible by the cameras 102; 2) the Fluoroscopy Registration Fixture is visible by the cameras 102; and 3) a valid fluoroscopic image was taken.

Figure 22:
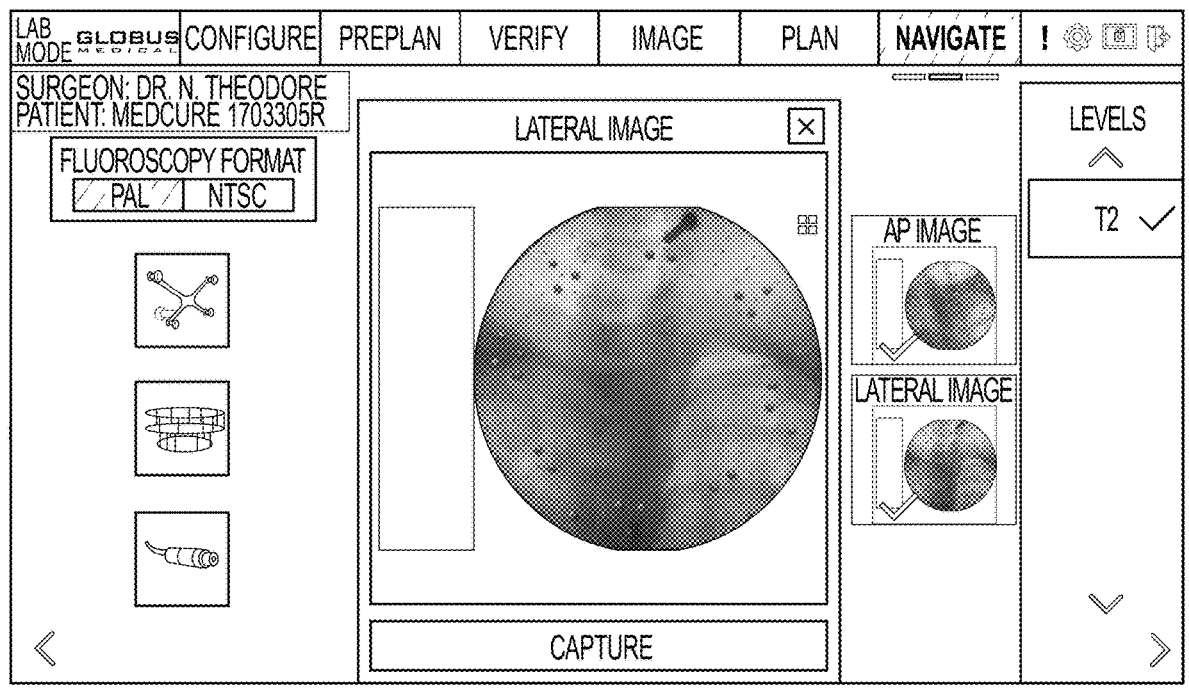
FIG. 22 illustrates an example user interface of image acquisition during a pre-operative CT imaging workflow according to some embodiments.

An example user interface is shown in FIG. 22 according to some embodiments. Each of the three images on the left of the screen turn to a defined color when ready for image capture. When all three conditions are met, the intra-operative fluoroscopic image is acquired and then the CAPTURE button is selected to transfer the image to the system. Once both images are successfully captured, the spinal level on the right side of the screen displays a check mark. The right arrows can be selected to advance to the next tab.

Figure 23:
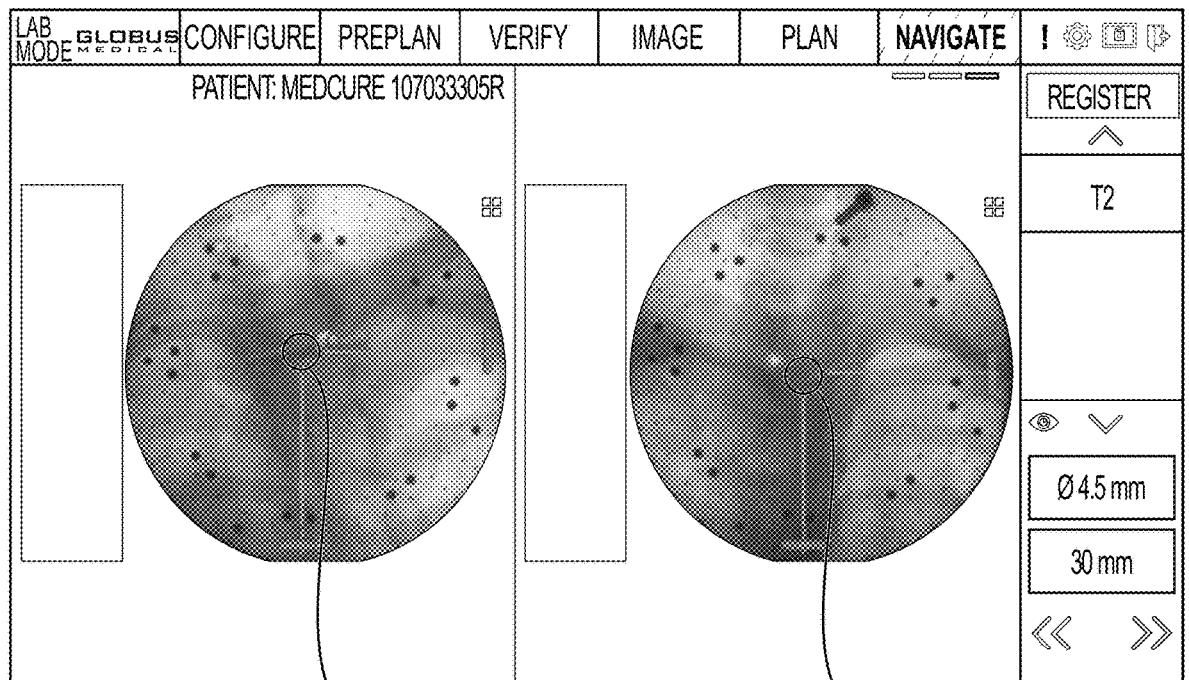
FIG. 23 illustrates an example user interface after level selection during a pre-operative CT imaging workflow according to some embodiments.

An example user interface for selecting a desired level is shown in FIG. 23 according to some embodiments. The planned screw may be dragged-and-dropped onto the fluoroscopic images. A displayed graphical object, e.g., circle 2300*a* and/or 2300*b*, can be controlled, via user input through a user interface, to roughly position the screw within the vertebral body. The user input may correspond to a user touch-selecting or clicking on a desired location on the display and/or providing steering commands through a keyboard. The screw shank is confirmed to be positioned correctly, with the head and tail of the screws in the desired direction, and with the left/right correctly oriented. The register button can be selected when the confirmation is complete to allow registration.

Figure 24:
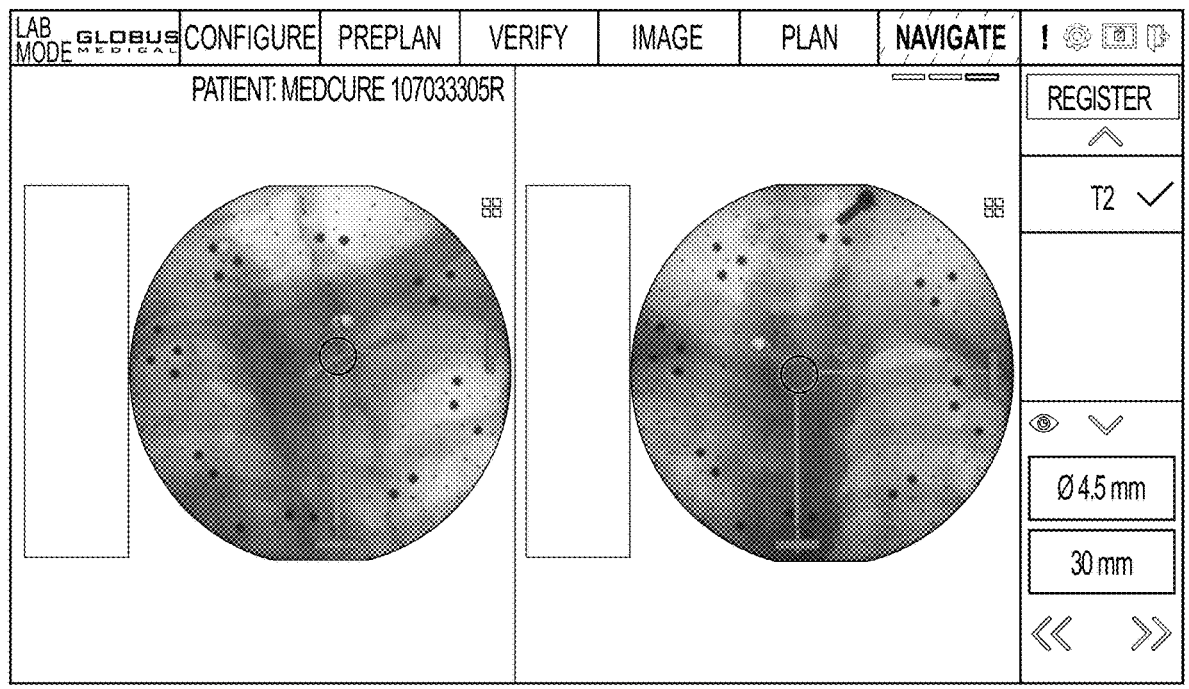
FIG. 24 illustrates an example user interface after successful registration during a pre-operative CT imaging workflow according to some embodiments.

A check mark is shown next to the active level when registration is successful. An example user interface is shown in FIG. 24 according to some embodiments. The right arrows are selected when registration is completed.

Figure 34:
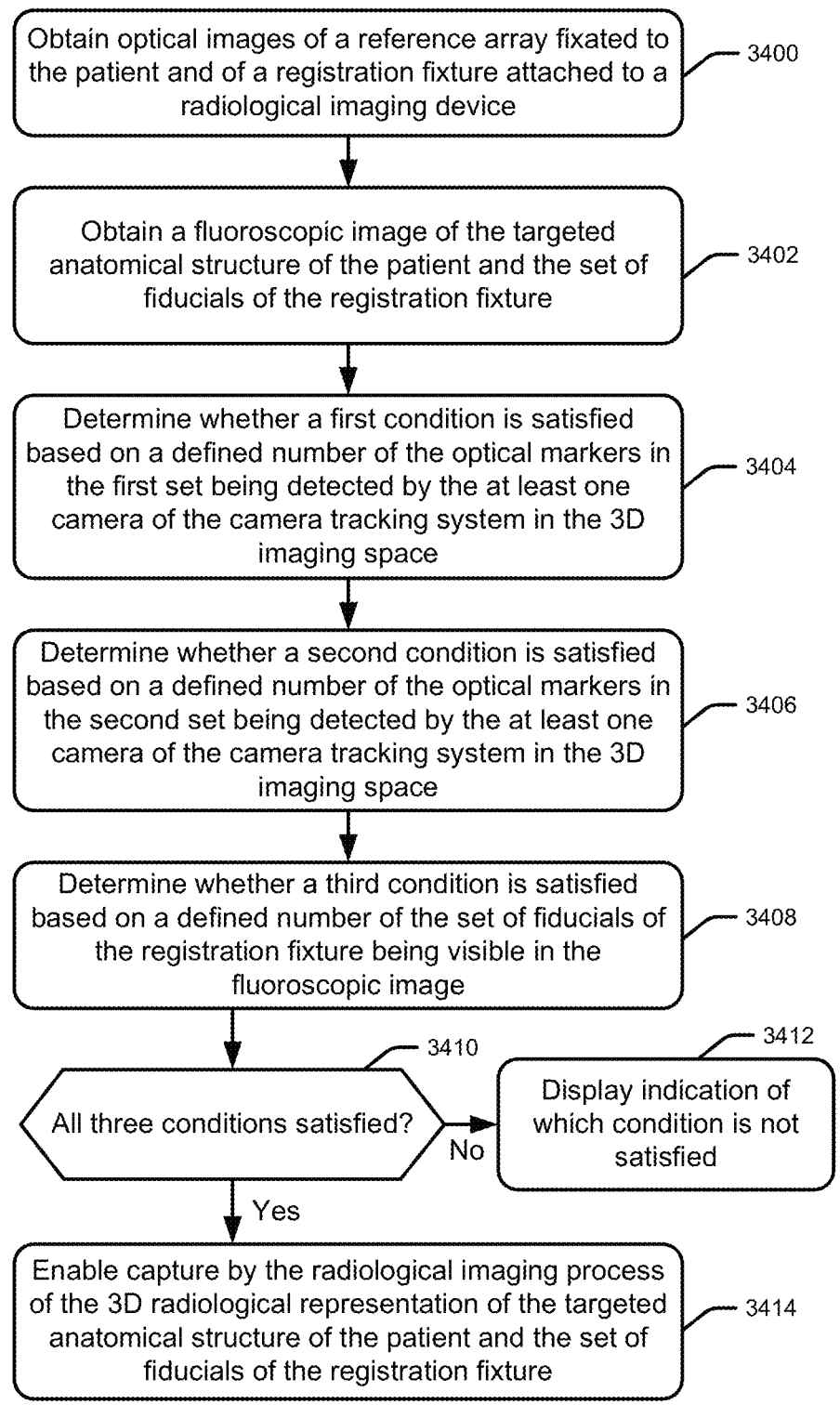

Corresponding operations that may be performed are now described in the context of FIG. 34. FIG. 34 illustrates operations that may be performed by the surgical system in accordance with some embodiments. Referring to FIG. 34, prior to obtaining the 3D radiological representation of the targeted anatomical structure of the patient and the set of fiducials of the registration fixture, the operations include to obtain 3400, from at least one camera of the camera tracking system, optical images of a reference array (e.g., DRB 900 in FIG. 9) fixated to the patient and of a registration fixture (e.g., fixture 2100 in FIG. 21) attached to a radiological imaging device, the reference array including a first set of optical markers detectable by the at least one camera of the camera tracking system in the 3D imaging space, and the registration fixture including a second set of optical markers detectable by the at least one camera of the camera tracking system in the 3D imaging space. The operations obtain 3402 a fluoroscopic image of the targeted anatomical structure of the patient and the set of fiducials of the registration fixture. The operations determine 3404 whether a first condition is satisfied based on a defined number of the optical markers in the first set being detected by the at least one camera of the camera tracking system in the 3D imaging space. The operations determine 3406 whether a second condition is satisfied based on a defined number of the optical markers in the second set being detected by the at least one camera of the camera tracking system in the 3D imaging space. The operations determine 3408 whether a third condition is satisfied based on a defined number of the set of fiducials of the registration fixture being visible in the fluoroscopic image. A determination 3410 is made whether any of the three conditions is not satisfied. When one of the first, second, and third conditions is not satisfied, the operations display 3412 an indication of the not satisfied one of the first, second, and third conditions, and inhibit capture by a radiological imaging process of the 3D radiological representation of the targeted anatomical structure of the patient and the set of fiducials of the registration fixture. In contrast, when each of the first, second, and third conditions are satisfied, the operations enable 3414 capture by the radiological imaging process of the 3D radiological representation of the targeted anatomical structure of the patient and the set of fiducials of the registration fixture.

The operations may trigger capture of anteroposterior and lateral fluoroscopic images at a plurality of defined locations of the targeted anatomical structure of the patient based on determining each of the first, second, and third conditions are satisfied. The operations may then compute the 3D radiological representation of the targeted anatomical structure of the patient and the set of fiducials of the registration fixture based on the captured anteroposterior and lateral fluoroscopic images at the plurality of defined locations of the targeted anatomical structure of the patient.

Landmark Check

After registration has been completed, a landmark check, or verification, can be performed to operationally ensure that the registration was calculated successfully. Using the verification probe, touch an anatomical landmark and verify that the corresponding location is shown on the system monitor. This process may be repeated using, e.g., 2 to 3 landmarks.

Navigation

Figure 25:
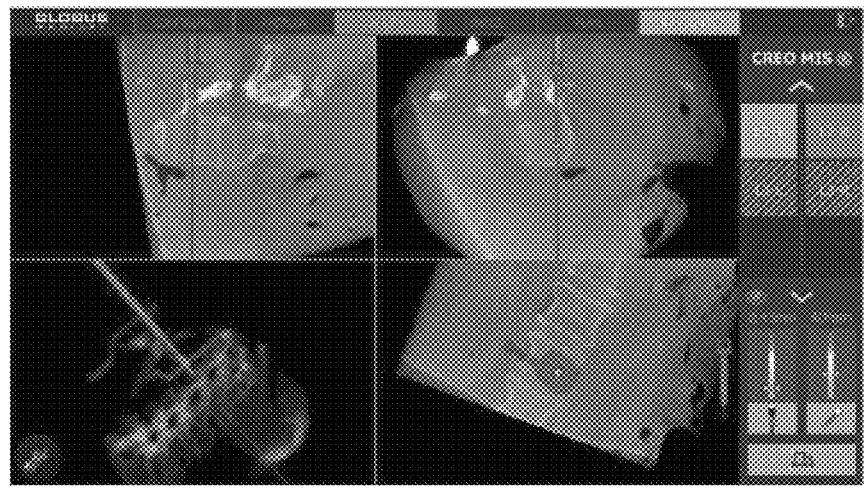
FIG. 25 illustrates an example user interface of a real-time instrument/implant trajectory and navigated instruments during a pre-operative CT imaging workflow according to some embodiments.

With reference to FIG. 25, the user selects the desired implant label on the right of the screen. The real-time instrument/implant trajectory (actual plan) is updated to be displayed on the patient images along with the planned screw, allowing the user to confirm the desired trajectory. If the real-time trajectory is not acceptable, the user can return to the PLAN tab to select another trajectory. If the real-time trajectory is acceptable, the user inserts the screw according to the instrument's current trajectory to the desired depth.

Navigated instruments are displayed as they are advanced to the planned position. While navigating the instruments, the user can repetitively observe the monitor and surgical site to ensure consistency between tactile and navigation feedback.

Corresponding operations by the surgical system may include to display the planned trajectory of virtual implant device as an overlay on the view of the 3D radiological representation of the targeted anatomical structure. The operations obtain, from at least one camera of the camera tracking system, optical images of a reference array fixated to a real-implant device corresponding to the virtual implant device, the reference array including a set of optical markers detectable by the at least one camera of the camera tracking system in the 3D imaging space. The operations track pose of the real-implant device in the 3D imaging space based on pose of the reference array in the optical images while the real implant device is being positioned by a user relative to the targeted anatomical structure of the patient. The operations display updated graphical representations of the real-implant device relative to the planned trajectory of the virtual implant device according to the tracked pose in the 3D imaging space.

Removing Registration Fixture

Carefully remove the Fluoroscopic Registration Fixture. Ensure the patient attachment instrument does not move.

Fluoroscopic Imaging Workflow

IMAGE Tab

Registration Setup

Figure 26:
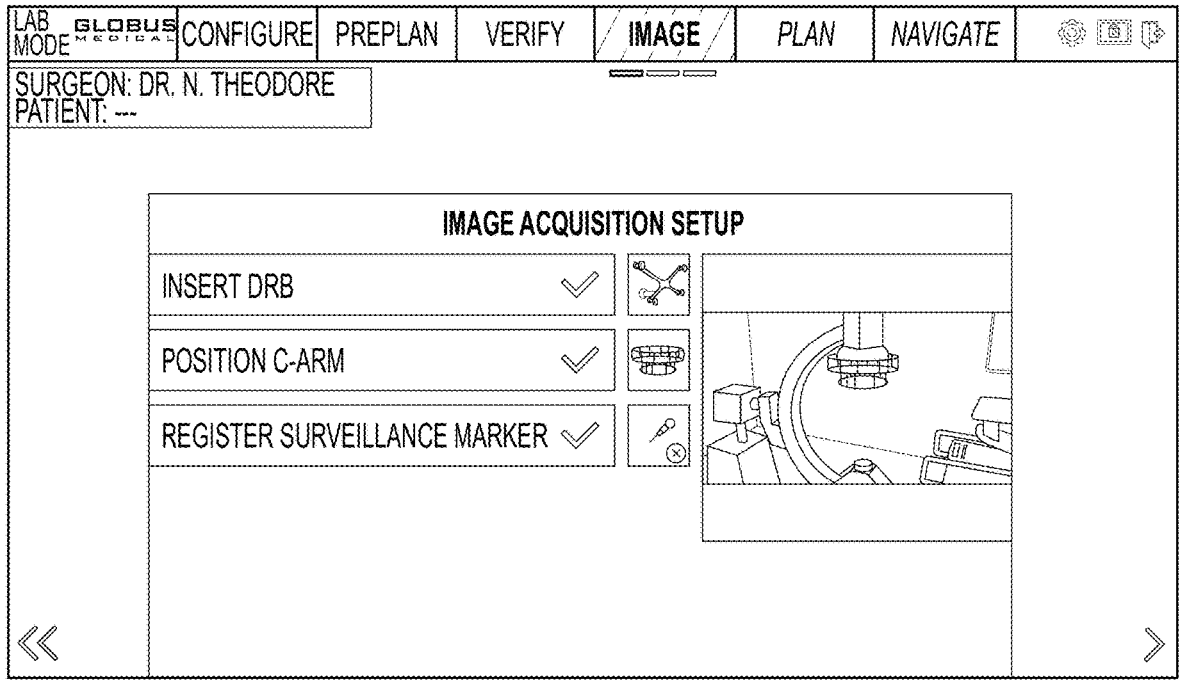
FIG. 26 illustrates an example user interface of the IMAGE tab during a fluoroscopic imaging workflow according to some embodiments.

One screen shown in FIG. 26, which may substantially correspond to the screen of FIG. 20, highlights the three steps to complete before fluoroscopic images can be taken to register the patient, such as described above for FIG. 20.

The Fluoroscopy Registration Fixture can be attached to the image intensifier on the C-arm, as shown in FIG. 21 according to some embodiments, by turning the clamp clockwise until tight. Install new optical markers on the fixture prior to orienting the fixture such that the optical markers are facing the camera.

The user ensures that the Dynamic Reference Base is still visible to the cameras 102 after the C-Arm is in place. The surveillance marker may be registered by placing an instrument close to the reflective sphere on the surveillance marker but not touching. The box turns to a defined color when it is activated. The right arrows can be selected to advance to the next tab.

Image Acquisition

Intra-operative fluoroscopic images are acquired, such as one AP and one lateral.

In some embodiments, the operations verify that the following three conditions are met prior to enable acquisition of the images: 1) the DRB is visible by the cameras 102; 2) the Fluoroscopy Registration Fixture is visible by the cameras 102; and 3) a valid fluoroscopic image was taken.

Figure 27:
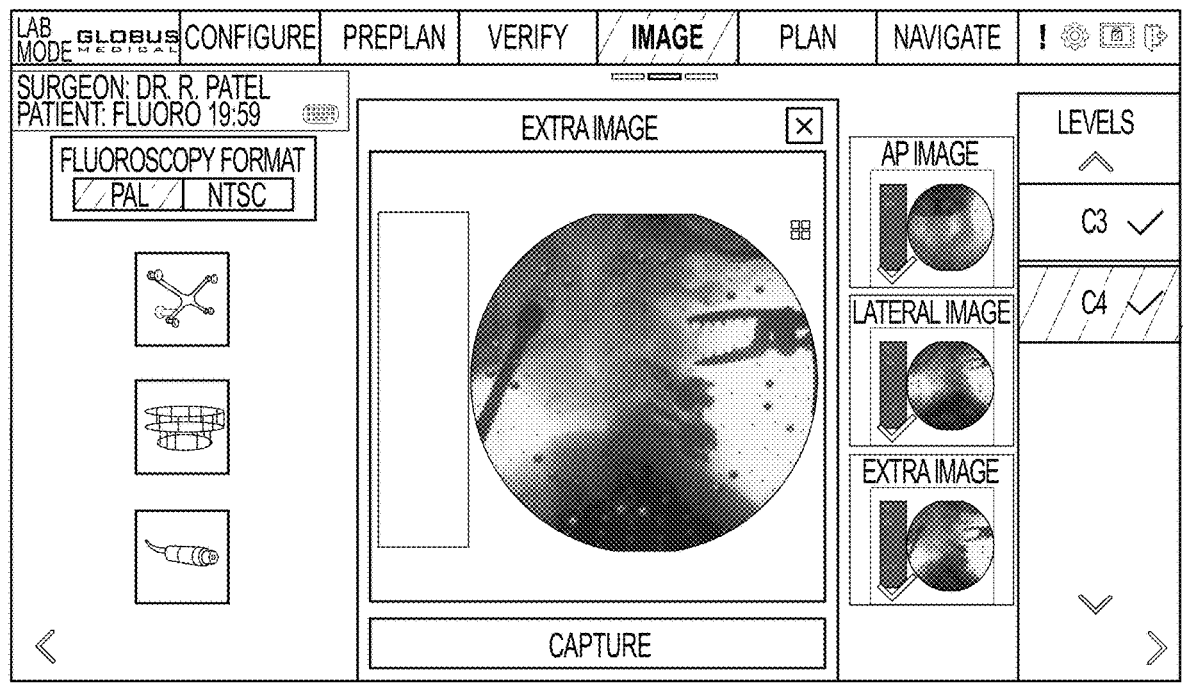
FIG. 27 illustrates an example user interface of image acquisition during a fluoroscopic imaging workflow according to some embodiments.

An example user interface is shown in FIG. 27 according to some embodiments. Each of the three images on the left of the screen turn to a defined color when ready for image capture. When all three conditions are met, the intra-operative fluoroscopic image is acquired and then the CAPTURE button is selected to transfer the image to the system. Once both images are successfully captured, the level on the right side of the screen displays a check mark. Once the appropriate images have been loaded and selected, the right arrows can be selected to proceed.

Landmark Check

After registration has been completed, a landmark check, or verification, can be performed to operationally ensure that the registration was calculated successfully. Using the navigated verification probe, touch an anatomical landmark and verify that the corresponding location is shown on the system monitor. This process may be repeated using, e.g., 2 to 3 landmarks.

Removing Registration Fixture

The Fluoroscopic Registration Fixture is removed while ensuring the patient attachment instrument does not move.

PLAN Tab

Figure 28:
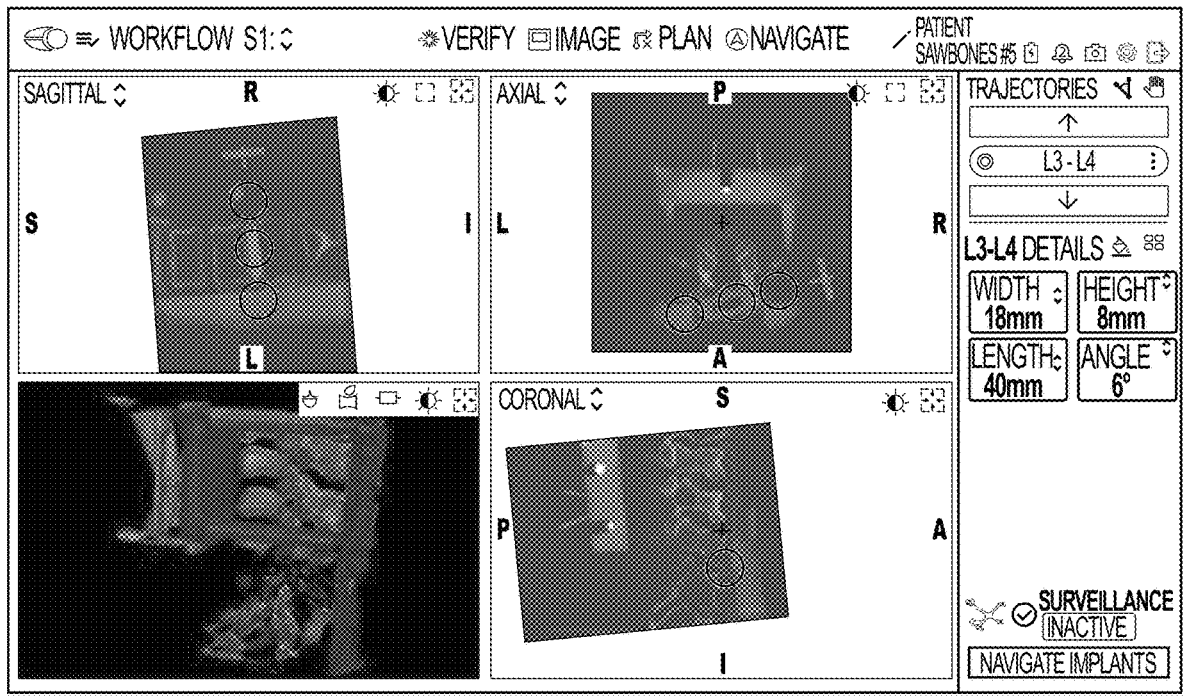
FIG. 28 illustrates an example user interface of the PLAN tab during a fluoroscopic imaging workflow according to some embodiments.

The PLAN tab allows the user to plan all screw trajectories and interbody placement on the patient image. An example user interface is shown in FIG. 28 according to some embodiments. Implants are preloaded on the right-hand side of the screen, based on selections made in the PREPLAN tab.

To add an implant onto the planning page, the user may drag and drop the appropriate implant label on the image at the desired slice. The active plan is shown in a defined color. Details of the active screw plan are shown on the lower right of the screen, including screw family, diameter, and length. A user may select (e.g., click) on the right arrows to advance to the next tab once plans are complete for all screws.

Once the implant is dropped on the image, the implant planning features are used to adjust implant location by, e.g., dragging the implant image on the touch screen. The selects the specific implant size (width, length, height, lordosis) on the right panel of the screen. Alternatively or additionally, software of the planning system may perform automatic adjustment of the implant location so that the dropped implant satisfies one or more defined rules with respect to anatomy in the image.

NAVIGATE Tab

Figure 29:
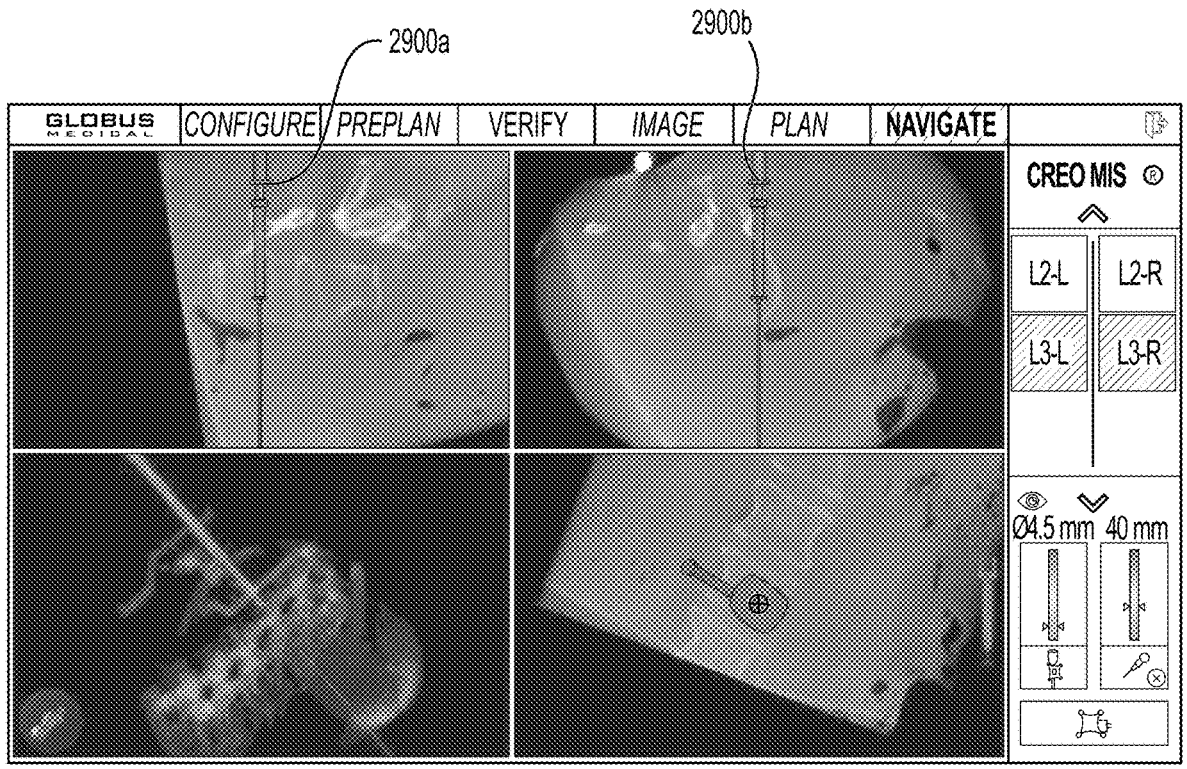
FIG. 29 illustrates an example user interface of the NAVIGATE tab during a fluoroscopic imaging workflow according to some embodiments.

The NAVIGATE tab allows the user to visualize the navigated instrument trajectory and the planned trajectory with respect to patient anatomy. An example user interface is shown in FIG. 29 according to some embodiments.

The user selects the desired implant label on the right of the screen. The real-time instrument/implant trajectory (actual plan) is updated to be displayed on the patient images along with the planned screw, e.g., as graphical objects 2900a and 2900b, allowing the user to confirm the desired trajectory. If the real-time trajectory is not acceptable, the user can return to the PLAN tab to select another trajectory. If the real-time trajectory is acceptable, the user inserts the screw according to the instrument's current trajectory to the desired depth.

Navigated instruments are displayed as they are advanced to the planned position. While navigating the instruments, the repetitively observes the monitor and surgical site to ensure consistency between tactile and navigation feedback.

Example Surgical Room Equipment Layout and Operation

Figure 30:
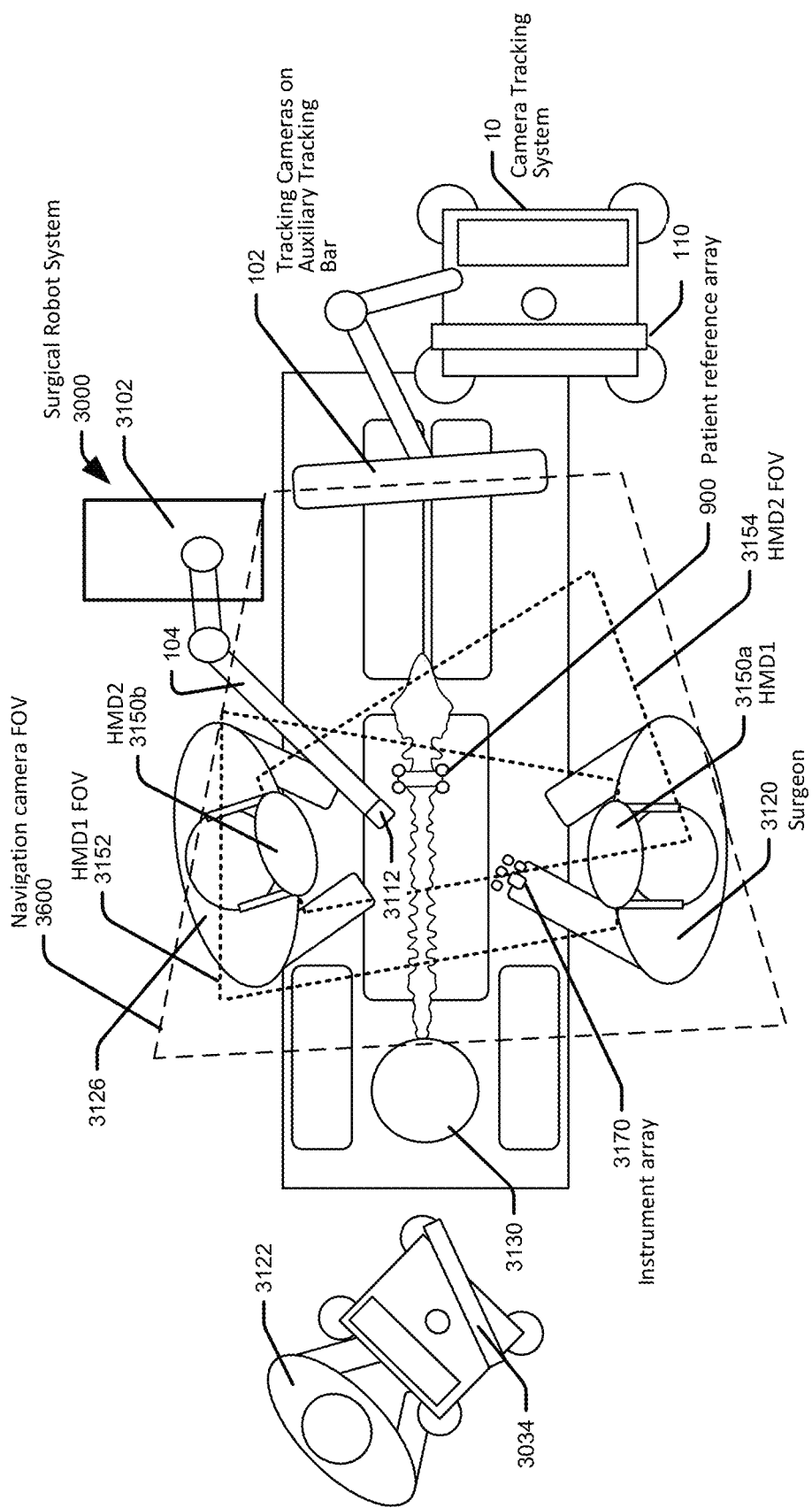
FIG. 30 is an overhead view of personnel optionally wearing extended reality (XR) headsets during a surgical procedure in a surgical room that includes a camera tracking system for navigated surgery and a surgical robot system for robotic assistance and configured in accordance with some embodiments.

FIG. 30 is an overhead view of personnel optionally wearing extended reality (XR) headsets 3150a-3150b during a surgical procedure in a surgical room that includes a camera tracking system 10 for navigated surgery and optionally includes a surgical robot system for robotic assistance, and each of which is configured in accordance with some embodiments.

Referring to FIG. 30, the robot system 3000 may include, for example, a surgical robot 3102, one or more robotic arms 104, an end-effector 3112, for example, configured to attach to a joint manipulation arm, and an end-effector reference array which can include one or more tracking markers. The robot system 3000 may further include one or more displays. The DRB 900 includes a plurality of tracking markers and is adapted to be secured directly to a patient 3130 (e.g., to a bone of the patient 3130). Another reference array 3170 is attached or formed on an instrument, etc. The camera tracking system 10 can have any suitable configuration to move, orient, and support the tracking cameras 102 in a desired position, and may contain a computer operable to track pose of reference arrays.

The tracking cameras 102 may include any suitable camera or cameras, such as one or more infrared cameras (e.g., bifocal or stereophotogrammetric cameras), able to identify, for example, active and passive tracking markers for various reference arrays attached as the patient 3130 (e.g., DRB 900), end-effector 3112 (end-effector reference array), instrument(s) (e.g., instrument array 3170), extended reality (XR) headset(s) 3150*a*-3150*b* worn by a surgeon 3120 and/or a surgical assistant 3126, etc. in a given measurement volume viewable from the perspective of the tracking cameras 102. The tracking cameras 102 may track markers attached or formed on the robot arm 140 manipulated by a user (surgeon) and/or the robot system 3000. The tracking cameras 102 may scan the given measurement volume and detect light that is emitted or reflected from the reference arrays in order to identify and determine poses of the reference arrays in three-dimensions. For example, active reference arrays may include infrared-emitting markers that are activated by an electrical signal (e.g., infrared light emitting diodes (LEDs)), and passive reference arrays may include retro-reflective markers that reflect infrared light (e.g., they reflect incoming IR radiation into the direction of the incoming light), for example, emitted by illuminators on the tracking cameras 102 or other suitable device.

The XR headsets 3150*a* and 3150*b* (also referred to as an XR headset 150) may each include tracking cameras that can track poses of reference arrays within their camera field-of-views (FOVs) 3152 and 3154, respectively. Accordingly, as illustrated in FIG. 30, the poses of reference arrays attached to various objects can be tracked while in the FOVs 3152 and 3154 of the XR headsets 3150*a* and 3150*b* and/or a FOV 3600 of the tracking cameras 102.

An XR headset may be configured to augment a real-world scene with computer generated XR images. The XR headset may be configured to provide an augmented reality (AR) viewing environment by displaying the computer generated XR images on a see-through display screen that allows light from the real-world scene to pass therethrough for combined viewing by the user. Alternatively, the XR headset may be configured to provide a virtual reality (VR) viewing environment by preventing or substantially preventing light from the real-world scene from being directly viewed by the user while the user is viewing the computer generated AR images on a display screen. An XR headset can be configured to provide both AR and VR viewing environments. Thus, the term XR headset can referred to as an AR headset or a VR headset.

FIG. 30 illustrates a potential configuration for the placement of the camera tracking system 10 and the surgical robot system 3000 (when present) in an operating room environment. Computer-aided navigated surgery can be provided by the camera tracking system 10 controlling the XR headsets 3150*a* and 3150*b*, the display 110, and/or the display 3034 to display surgical procedure navigation information. Including the surgical robot system 3000 in an operating room is optional for computer-aided navigated surgery.

The camera tracking system 10 may use tracking information and other information from the camera tracking system 10 along with other tracking information and information from one or more XR headsets 3150*a* and 3150*b*, e.g., inertial tracking information and optical tracking information as well as (optional) microphone information. The XR headsets 3150*a* and 3150*b* operate to display visual information and may play-out audio information to the wearer. This information can be from local sources (e.g., the surgical robot 3102 and/or other operating room equipment), remote sources (e.g., patient medical image server), and/or other electronic equipment. The XR headsets 3150*a* and 3150*b* may be used to track poses of instruments, patient references, and/or a robot end-effector in 6 degrees-of-freedom (6DOF), and may track the hands of the wearer. The XR headsets 3150*a* and 3150*b* may also operate to track hand poses and gestures to enable gesture-based interactions with "virtual" buttons and interfaces displayed through the XR headsets 3150*a* and 3150*b* and may interpret hand or finger pointing or gesturing as triggering operation of various defined commands. Additionally, the XR headsets 3150*a* and 3150*b* may have a 1-10× magnification digital color camera sensor called a digital loupe.

An "outside-in" machine vision navigation bar (tracking cameras 102) may track pose of the joint manipulation arm using monochrome and/or color camera(s). The machine vision navigation bar generally has a more stable view of the environment because it does not move as often or as quickly as the XR headsets 3150*a* and 3150*b* tend to move while positioned on wearers' heads. The patient reference array 900 is generally rigidly attached to the patient with stable pitch and roll relative to gravity. This local rigid patient reference 900 can serve as a common reference for reference frames relative to other tracked arrays, such as a reference array on the end-effector 3112, instrument reference array 3170, and reference arrays on the XR headsets 3150*a* and 3150*b*.

In some embodiments, one or more of the XR headsets 3150*a* and 3150*b* are minimalistic XR headsets that display local or remote information but include fewer sensors and are therefore more lightweight.

The robot system 3000 may be positioned near or next to patient 3130. The tracking camera 102 may be separated from the robot system 3000 and positioned at the foot of patient 3130. This location allows the tracking camera 102 to have a direct visual line of sight to the surgical field 208. It is contemplated that the robot system 3000 and the tracking camera 102 will be located at any suitable position. In the configuration shown, the surgeon 3120 may be positioned across from the robot 3102, but is still able to manipulate the end-effector 3112 (and joint manipulation arm) and the display 110. A surgical assistant 3126 may be positioned across from the surgeon 3120 again with access to both the end-effector 3112 and the display 110. If desired, the locations of the surgeon 3120 and the assistant 3126 may be reversed. The traditional areas for the anesthesiologist 3122 and the nurse or scrub tech 124 remain unimpeded by the locations of the robot 3102 and camera 102. The anesthesiologist 3122 can operate anesthesia equipment which can include a display 3034.

The end-effector 3112 may be releasably coupled to the robotic arm 104 and movement of the end-effector 3112 can be controlled by at least one motor based on input from the camera tracking system 10. In some embodiments, the end-effector 3112 can be connectable to a joint manipulation arm 104 and may include a guide tube 114 configured to receive and orient a surgical instrument, tool, or implant used to perform a surgical procedure on the patient 3130.

As used herein, the term "end-effector" is used interchangeably with the terms "end-effectuator" and "effectuator element." The term "instrument" is used in a non-limiting manner and can be used interchangeably with "tool" and "implant" to generally refer to any type of device that can be used during a surgical procedure in accordance with embodiments disclosed herein. Example instruments, tools, and implants include, without limitation, joint manipulation arms, drills, screwdrivers, saws, dilators, retractors, probes, implant inserters, and implant devices such as screws, spacers, interbody fusion devices, plates, rods, etc. In some embodiments, the end-effector 3112 can comprise any structure for effecting the movement of a surgical instrument in a desired manner.

The surgical robot 3102 is operable to control the translation and orientation of the end-effector 3112. The robot 3102 may be operable to move end-effector 3112 under computer control along x-, y-, and z-axes, for example. The end-effector 3112 can be configured for selective rotation under computer control about one or more of the x-, y-, and z-axis, and a Z Frame axis (such that one or more of the Euler Angles (e.g., roll, pitch, and/or yaw) associated with end-effector 3112 can be selectively computer controlled). In some embodiments, selective control of the translation and orientation of end-effector 3112 can permit performance of medical procedures with significantly improved accuracy compared to conventional robots that utilize, for example, a six degree of freedom robotic arm comprising only rotational axes. For example, the surgical robot system 3000 may be used to operate on patient 3130, and robotic arm 104 can be positioned above the body of patient 3130, with end-effector 3112 selectively angled relative to the z-axis toward the body of patient 3130.

In some example embodiments, the XR headsets 3150a and 3150b can be controlled to dynamically display an updated graphical indication of the pose of the surgical instrument so that the user can be aware of the pose of the surgical instrument at all times during the procedure.

As used herein, the term "pose" refers to the position and/or the rotational angle of one object (e.g., dynamic reference array, end-effector, surgical instrument, anatomical structure, etc.) relative to another object and/or to a defined coordinate system. A pose may therefore be defined based on only the multidimensional position of one object relative to another object and/or relative to a defined coordinate system, based on only the multidimensional rotational angles of the object relative to another object and/or to a defined coordinate system, or based on a combination of the multidimensional position and the multidimensional rotational angles. The term "pose" therefore is used to refer to position, rotational angle, or combination thereof.

In some further embodiments, the surgical robot 3102 can be configured to correct the path of the joint manipulation arm being moved by the surgeon with guidance by the robotic arm 104. In some example embodiments, surgical robot 3102 can be configured to perform stoppage, modification, and/or manual control of the movement of end-effector 3112. Thus, in use, in example embodiments, a surgeon or other user can operate the system 3000, and has the option to stop, modify, or manually control the autonomous movement of end-effector 3112.

Reference arrays can be formed on or connected to the robotic arm 104, the end-effector 3112, patient 3130, and/or the surgical instrument. The camera tracking system 10 can track poses of the reference arrays in, e.g., 6 degree-of-freedom (e.g., position along 3 orthogonal axes and rotation about the axes). In some embodiments, a reference array including a plurality of tracking markers can be provided thereon (e.g., formed-on or connected-to) to an outer surface of the robot 3102, such as on the robot arm 104 and/or on the end-effector 3112. A patient reference array 900 including one or more tracking markers can further be provided on the patient 3130 (e.g., formed-on or connected-to). An instrument reference array 3170 including one or more tracking markers can be provided on surgical instruments (e.g., a screwdriver, dilator, implant inserter, or the like). The reference arrays enable each of the marked objects (e.g., the end-effector 3112, the patient 3130, and the surgical instruments) to be tracked by the camera tracking system 10, and the tracked poses can be used to provide navigation guidance to a user for performance of a surgical procedure and/or can be used to control movement of the surgical robot 3102 for guiding the end-effector 3112.

Example Surgical System:

FIG. 31 illustrates a block diagram of surgical system which includes a camera tracking system 10 and navigation system 3604, and further optionally includes a surgical robot 3102, imaging device(s) 3620, and an XR headset 3150, which are each operative in accordance with some embodiments.

The imaging devices 3620 may include a C-arm imaging device, an O-arm imaging device, and/or a patient image database. A computer platform 3600 includes at least one processor, at least one memory storing program instructions executable by the at least one processor to perform operations. The computer platform 3600 may perform operations of the camera tracking system 10 and/or the navigation system 3604. The XR headset 3150 provides an improved human interface for performing navigated surgical procedures. The XR headset 3150 can be configured to provide functionalities, e.g., via the computer platform 3600, that include without limitation any one or more of: display camera tracking information and surgical procedure navigation information, identify hand gesture-based commands, etc. A display device 3112 may include a video projector, flat panel display, etc. The user can view XR graphical objects as an overlay anchored to particular real-world objects viewed through a see-through display screen. The XR headset 3150 may additionally or alternatively be configured to display on the display device 3112 video streams from cameras mounted to one or more XR headsets 3150 and other cameras, and/or medical images obtained from the imaging device(s) 3620.

Electrical components of the XR headset 3150 can include a plurality of cameras 3122, a microphone 3121, a gesture sensor 3108, a pose sensor (e.g., inertial measurement unit (IMU)) 3116, the display device 3112, and a wireless/wired communication interface 3124. The cameras 3122 of the XR headset 3150 may be visible light capturing cameras, near infrared capturing cameras, or a combination of both.

The cameras 3122 may be configured to operate as the gesture sensor 3108 by tracking user hand gestures performed within the field of view of the camera(s) 3122. Alternatively, the gesture sensor 3108 may be a proximity sensor and/or a touch sensor that senses hand gestures performed proximately to the gesture sensor 3108 and/or senses physical contact, e.g. tapping on the sensor 3108 or its enclosure. The pose sensor 3116, e.g., IMU, may include a multi-axis accelerometer, a tilt sensor, and/or another sensor that can sense rotation and/or acceleration of the XR headset 3150 along one or more defined coordinate axes. Some or all of these electrical components may be contained in a head-worn component enclosure or may be contained in another enclosure configured to be worn elsewhere, such as on the hip or shoulder.

As explained above, a surgical system includes a camera tracking system 10 which may be part of the computer platform 3600 which may also provide functionality of the navigation system 3604 and/or of the XR headset controller 3110. The surgical system may include the imaging devices and/or the surgical robot 3102. The navigation system 3604 can be configured to provide visual navigation guidance to an operator for moving and positioning an instrument relative and/or an end effector relative to patient anatomy (e.g., relative to the DRB 900) based on a surgical plan, e.g., from a surgical planning function, defining where a surgical procedure is to be performed using the instrument on the anatomy and based on a pose of the anatomy determined by the camera tracking system 10. The navigation system 3604 may be further configured to generate navigation information based on a target pose for the instrument, a present pose of the patient anatomy, and a present pose of the instrument and/or an end-effector of the surgical robot 3102, where the steering information is used to display information through the XR headset 3150 and/or another display to indicate where the instrument and/or the end-effector of the surgical robot 3102 should be moved to perform the surgical plan.

The electrical components of the XR headset 3150 can be operatively connected to the electrical components of the computer platform 3600 through a wired/wireless interface 3124. The electrical components of the XR headset 3150 may be operatively connected, e.g., through the computer platform 3600 or directly connected, to various imaging devices 3620, e.g., the C-arm imaging device, the I/O-arm imaging device, the patient image database, and/or to other medical equipment through the wired/wireless interface 3124.

The surgical system further includes at least one XR headset controller 3110 that may reside in the XR headset 3150, the computer platform 3600, and/or in another system component connected via wired cables and/or wireless communication links. Various functionality is provided by software executed by the XR headset controller 3110. The XR headset controller 3110 is configured to receive information from the camera tracking system 10 and the navigation controller 3604, and to generate an XR objects based on the information for display on the display device 3112.

The XR headset controller 3110 can be configured to operationally process signaling from the cameras 3122, the microphone 3121, and/or the pose sensor 3116, and be connected to display XR images on the display device 3112 for user viewing. Thus, the XR headset controller 3110 illustrated as a circuit block within the XR headset 3150 is to be understood as being operationally connected to other illustrated components of the XR headset 3150 but not necessarily residing within a common housing or being otherwise transportable by the user. For example, the XR headset controller 3110 may reside within the computer platform 3600 which, in turn, may reside within a housing of the surgical robot 3102, the camera tracking system 10, etc.

Further Definitions and Embodiments:

In the above-description of various embodiments of the present disclosure, aspects of the present disclosure may be illustrated and described herein in any of a number of patentable classes or contexts including any new and useful process, machine, manufacture, or composition of matter, or any new and useful improvement thereof. Accordingly, aspects of the present disclosure may be implemented in entirely hardware, entirely software (including firmware, resident software, micro-code, etc.) or combining software and hardware implementation that may all generally be referred to herein as a "circuit," "module," "component," or "system." Furthermore, aspects of the present disclosure may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing.

More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

It is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

The flowchart and block diagrams in the figures illustrate the architecture, functionality, and operation of possible implementations of systems, methods, and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

The corresponding structures, materials, acts, and equivalents of any means or step plus function elements in the claims below are intended to include any disclosed structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

What is claimed is:

1. A surgical system for computer assisted navigation during surgery, the surgical system comprising:
    a camera tracking system including one or more cameras;
    a display assembly; and
    a housing base assembly including a processing platform having a memory, a user interface, communication circuitry configured to communicate with the camera tracking system and the display assembly, and at least one processor configured to:
        obtain a three-dimensional (3D) radiological representation of a targeted anatomical structure of a patient containing a set of radiopaque fiducials of a registration fixture, the 3D radiological representation being derived from a 3D scan of the patient with a radiologic imaging device;
        attempt to register locations of the set of fiducials contained in the 3D radiological representation to a 3D imaging space tracked by the camera tracking system;
        based on determining that one of the fiducials of the set has a location that was not successfully registered to the 3D imaging space,
        display, via the display assembly, at least one two-dimensional (2D) view of the 3D radiological representation with a graphical overlay indicating that the fiducial has not been successfully registered to the 3D imaging space,
        receive user-supplied location information, via the user interface, identifying where the fiducial is located in the displayed 2D view of the 3D radiological representation, and
        register the location of the fiducial to the 3D imaging space based on the user-supplied location information; and
        obtain, from at least one camera of the camera tracking system, optical images of a reference array fixated to the patient and of the registration fixture, the reference array including a first set of optical markers detectable by the at least one camera of the camera tracking system in the 3D imaging space, and the registration fixture including a second set of optical markers detectable by the at least one camera of the camera tracking system in the 3D imaging space;
    wherein the operation to receive user-supplied location information identifying where the fiducial is located in the 3D radiological representation, comprises to:
        display three orthogonal views of the fiducial in the 3D radiological representation and/or the 3D imaging space;
        display a graphical object overlaid on an initial location in the three orthogonal views;

move location of where the graphical object is displayed in the three orthogonal views responsive to input from the user through a user interface;

determine location of the fiducial in the 3D radiological representation and/or the 3D imaging space based on the location of where the graphical object is displayed in the three orthogonal views; and the operation to register the location of the fiducial to the 3D imaging space is based on the determined location of the fiducial in the 3D radiological representation;

wherein the operation to display the graphical object overlaid on the initial location in the three orthogonal views, comprises:

determining the initial location to correspond to a predicted location of the fiducial based on relative locations of fiducials defined by a registration fixture template.

2. The surgical system of claim 1, wherein the at least one processor is further operative to move the location where the graphical object is displayed in the three orthogonal views to track directional inputs received through the user interface of the surgical system.

3. The surgical system of claim 1, wherein the at least one processor is further operative to:

track locations of a tool captured in video from a camera of the camera tracking system while the tool is being moved by a user toward one of the fiducials that was successfully registered to the 3D image space;

display updated representations of the tool according to the tracked locations in the 3D imaging space; and confirm registration accuracy of the one of the fiducials that was successfully registered to the 3D image space based on comparison of a designated one of the tracked locations of the tool to the location of the one of the fiducials registered to the 3D image space.

4. The surgical system of claim 1, wherein the operation to attempt to register locations of the set of fiducials in the 3D radiological representation to the 3D imaging space tracked by the camera tracking system, comprises:

obtain, from at least one camera of the camera tracking system, an optical image of a reference array fixated to the patient, the reference array including a set of optical markers detectable by the at least one camera of the camera tracking system in the 3D imaging space;

attempt to register locations of a pattern of the set of optical markers to locations of a pattern of the set of fiducials in the 3D radiological representation; and identify any of the optical markers of the reference array that are not successfully registered to any of the fiducials of the registration fixture.

5. The surgical system of claim 1, wherein the operations further comprise to:

display a virtual implant device as an overlay on a view of the 3D radiological representation of the targeted anatomical structure;

display a graphical indication of a trajectory of the virtual implant device representing an implantation trajectory of the virtual implant device into the targeted anatomical structure;

update pose of the graphical indication of the trajectory of the virtual implant device displayed in the view of the 3D radiological representation, to track steering inputs received through a user interface of the surgical system; and store as a planned trajectory of the virtual implant device, a user-designated one of the poses of the graphical indication of the trajectory.

6. The surgical system of claim 5, wherein the operations further comprise to:

display a set of implant devices which are selectable by a user for implant planning; and generate a graphical representation of the virtual implant device based on a template of one of the set of user-selectable implant devices which is selected by a user through the user interface.

7. The surgical system of claim 5, wherein the operations further comprise to:

display the planned trajectory of virtual implant device as an overlay on the view of the 3D radiological representation of the targeted anatomical structure;

obtain, from at least one camera of the camera tracking system, optical images of a reference array fixated to a real-implant device corresponding to the virtual implant device, the reference array including a set of optical markers detectable by the at least one camera of the camera tracking system in the 3D imaging space;

track pose of the real-implant device in the 3D imaging space based on pose of the reference array in the optical images while the real implant device is being positioned by a user relative to the targeted anatomical structure of the patient; and display updated graphical representations of the real-implant device relative to the planned trajectory of the virtual implant device according to the tracked pose in the 3D imaging space.

8. The surgical system of claim 1, wherein prior to obtaining the 3D radiological representation of the targeted anatomical structure of the patient and the set of fiducials of the registration fixture, the at least one processor is further operative to:

obtain a fluoroscopic image of the targeted anatomical structure of the patient and the set of fiducials of the registration fixture;

determine whether a first condition is satisfied based on a defined number of the optical markers in the first set being detected by the at least one camera of the camera tracking system in the 3D imaging space;

determine whether a second condition is satisfied based on a defined number of the optical markers in the second set being detected by the at least one camera of the camera tracking system in the 3D imaging space;

determine whether a third condition is satisfied based on a defined number of the set of fiducials of the registration fixture being visible in the fluoroscopic image;

when one of the first, second, and third conditions is not satisfied, display an indication of the not satisfied one of the first, second, and third conditions, and inhibit capture by a radiological imaging process of the 3D radiological representation of the targeted anatomical structure of the patient and the set of fiducials of the registration fixture; and when each of the first, second, and third conditions are satisfied, enable capture by the radiological imaging process of the 3D radiological representation of the targeted anatomical structure of the patient and the set of fiducials of the registration fixture.

9. The surgical system of claim 8, wherein the at least one processor is further operative to:

trigger capture of anteroposterior and lateral fluoroscopic images at a plurality of defined locations of the targeted anatomical structure of the patient based on determining each of the first, second, and third conditions are satisfied; and compute the 3D radiological representation of the targeted anatomical structure of the patient and the set of fiducials of the registration fixture based on the captured anteroposterior and lateral fluoroscopic images at the plurality of defined locations of the targeted anatomical structure of the patient.

10. A method by a surgical system for computer assisted navigation during surgery, the method comprising:

providing the surgical system for computer assisted navigation during surgery, the system including:
a camera tracking system including one or more cameras;
a display assembly; and
a housing base assembly including a processing platform having a memory, a user interface, communication circuitry configured to communicate with the camera tracking system and the display assembly, and at least one processor;

obtaining a three-dimensional (3D) radiological representation of a targeted anatomical structure of a patient containing a set of fiducials of a registration fixture;

attempting to register locations of the set of fiducials contained in the 3D radiological representation to a 3D imaging space tracked by the camera tracking system;

based on determining that one of the fiducials of the set has a location that was not successfully registered to the 3D imaging space, displaying, via the display device, at least one two-dimensional (2D) view of the 3D radiological representation with a graphical overlay indicating that the fiducial has not been successfully registered to the 3D imaging space, receiving user-supplied location information, via the user interface, identifying where the fiducial is located in the displayed 2D view of the 3D radiological representation, and registering the location of the fiducial to the 3D imaging space based on the user-supplied location information; and obtaining, from at least one camera of the camera tracking system, optical images of a reference array fixated to the patient and of the registration fixture, the reference array including a first set of optical markers detectable by the at least one camera of the camera tracking system in the 3D imaging space, and the registration fixture including a second set of optical markers detectable by the at least one camera of the camera tracking system in the 3D imaging space;

wherein: the receiving user-supplied location information identifying where the fiducial is located in the 3D radiological representation, comprises:

displaying three orthogonal views of the fiducial in the 3D radiological representation and/or the 3D imaging space;

displaying a graphical object overlaid on an initial location in the three orthogonal views;

moving location of where the graphical object is displayed in the three orthogonal views responsive to input from the user through a user interface;

determining location of the fiducial in the 3D radiological representation and/or the 3D imaging space based on the location of where the graphical object is displayed in the three orthogonal views; and the registering the location of the fiducial to the 3D imaging space is performed based on the determined location of the fiducial in the 3D radiological representation;

wherein the operation to display the graphical object overlaid on the initial location in the three orthogonal views, comprises:

determining the initial location to correspond to a predicted location of the fiducial based on relative locations of fiducials defined by a registration fixture template.

11. The method of claim 10, further comprising:

tracking locations of a tool captured in video from a camera of the camera tracking system while the tool is being moved by a user toward one of the fiducials that was successfully registered to the 3D image space;

displaying updated representations of the tool according to the tracked locations in the 3D imaging space; and confirming registration accuracy of the one of the fiducials that was successfully registered to the 3D image space based on comparison of a designated one of the tracked locations of the tool to the location of the one of the fiducials registered to the 3D image space.

12. The method of claim 10, wherein the attempting to register locations of the set of fiducials in the 3D radiological representation to the 3D imaging space tracked by the camera tracking system, comprises:

obtaining, from at least one camera of the camera tracking system, an optical image of a reference array fixated to the patient, the reference array including a set of optical markers detectable by the at least one camera of the camera tracking system in the 3D imaging space;

attempting to register locations of a pattern of the set of optical markers to locations of a pattern of the set of fiducials in the 3D radiological representation; and identifying any of the optical markers of the reference array that are not successfully registered to any of the fiducials of the registration fixture.

13. The method of claim 10, further comprising:

displaying a virtual implant device as an overlay on a view of the 3D radiological representation of the targeted anatomical structure;

displaying a graphical indication of a trajectory of the virtual implant device representing an implantation trajectory of the virtual implant device into the targeted anatomical structure;

updating pose of the graphical indication of the trajectory of the virtual implant device displayed in the view of the 3D radiological representation, to track steering inputs received through a user interface of the surgical system; and storing as a planned trajectory of the virtual implant device, a user-designated one of the poses of the graphical indication of the trajectory.

14. The method of claim 10, further comprising:

displaying a set of implant devices which are selectable by a user for implant planning; and generating a graphical representation of the virtual implant device based on a template of one of the set of user-selectable implant devices which is selected by a user through the user interface.

15. The method of claim 10, further comprising:

displaying the planned trajectory of virtual implant device as an overlay on the view of the 3D radiological representation of the targeted anatomical structure;

obtaining, from at least one camera of the camera tracking system, optical images of a reference array fixated to a real-implant device corresponding to the virtual implant device, the reference array including a set of optical markers detectable by the at least one camera of the camera tracking system in the 3D imaging space;

tracking pose of the real-implant device in the 3D imaging space based on pose of the reference array in the optical images while the real implant device is being positioned by a user relative to the targeted anatomical structure of the patient; and displaying updated graphical representations of the real-implant device relative to the planned trajectory of the virtual implant device according to the tracked pose in the 3D imaging space.

16. The method of claim 10, further comprising, prior to obtaining the 3D radiological representation of the targeted anatomical structure of the patient and the set of fiducials of the registration fixture:

obtaining a fluoroscopic image of the targeted anatomical structure of the patient and the set of fiducials of the registration fixture;

determining whether a first condition is satisfied based on a defined number of the optical markers in the first set being detected by the at least one camera of the camera tracking system in the 3D imaging space;

determining whether a second condition is satisfied based on a defined number of the optical markers in the second set being detected by the at least one camera of the camera tracking system in the 3D imaging space;

determining whether a third condition is satisfied based on a defined number of the set of fiducials of the registration fixture being visible in the fluoroscopic image;

when one of the first, second, and third conditions is not satisfied, displaying an indication of the not satisfied one of the first, second, and third conditions, and inhibiting capture by a radiological imaging process of the 3D radiological representation of the targeted anatomical structure of the patient and the set of fiducials of the registration fixture; and when each of the first, second, and third conditions are satisfied, enabling capture by the radiological imaging process of the 3D radiological representation of the targeted anatomical structure of the patient and the set of fiducials of the registration fixture.

17. The method of claim 16, further comprising:

triggering capture of anteroposterior and lateral fluoroscopic images at a plurality of defined locations of the targeted anatomical structure of the patient based on determining each of the first, second, and third conditions are satisfied; and computing the 3D radiological representation of the targeted anatomical structure of the patient and the set of fiducials of the registration fixture based on the captured anteroposterior and lateral fluoroscopic images at the plurality of defined locations of the targeted anatomical structure of the patient.

* * * * *